(12) United States Patent
Woods et al.

(10) Patent No.: US 11,697,799 B2
(45) Date of Patent: *Jul. 11, 2023

(54) SYSTEM AND METHOD FOR EXTRACTION AND CRYOPRESERVATION OF BONE MARROW

(71) Applicant: Ossium Health, Inc., San Francisco, CA (US)

(72) Inventors: Erik John Woods, Carmel, IN (US); Brian H. Johnstone, Fishers, IN (US); Dongsheng Gu, Indianapolis, IN (US); Aubrey Marie Sherry, Carmel, IN (US); Kelsey Gwen Musall, Avon, IN (US); John R. Woods, Indianapolis, IN (US); James Hardin, Columbia, SC (US); Alan Hooks, Commerce City, CO (US)

(73) Assignee: Ossium Health, Inc., San Francisco, CA (US)

( * ) Notice: Subject to any disclaimer, the term of this patent is extended or adjusted under 35 U.S.C. 154(b) by 506 days.

This patent is subject to a terminal disclaimer.

(21) Appl. No.: 16/734,713

(22) Filed: Jan. 6, 2020

(65) Prior Publication Data

US 2020/0325451 A1    Oct. 15, 2020

Related U.S. Application Data

(60) Provisional application No. 62/938,480, filed on Nov. 21, 2019, provisional application No. 62/834,087, filed on Apr. 15, 2019.

(51) Int. Cl.
*C12N 5/0775* (2010.01)
*A61B 17/16* (2006.01)
*A01N 1/02* (2006.01)
*A61B 17/00* (2006.01)

(52) U.S. Cl.
CPC ......... *C12N 5/0663* (2013.01); *A01N 1/0221* (2013.01); *A61B 17/1611* (2013.01); *A61B 2017/00831* (2013.01)

(58) Field of Classification Search
None
See application file for complete search history.

(56) References Cited

U.S. PATENT DOCUMENTS

| | | | |
|---|---|---|---|
| 4,674,184 A | 6/1987 | Anderson |
| 4,710,472 A | 12/1987 | Saur et al. |
| 5,474,687 A | 12/1995 | Van Vlasselaer |
| 5,672,346 A | 9/1997 | Srour et al. |
| 5,766,944 A | 6/1998 | Ruiz |
| 5,840,580 A | 11/1998 | Terstappen et al. |
| 5,858,782 A | 1/1999 | Long et al. |
| 6,739,112 B1 | 5/2004 | Marino |
| 6,900,029 B1 | 5/2005 | Coulter et al. |
| 7,470,538 B2 | 12/2008 | Laughlin et al. |
| 7,547,210 B1 | 6/2009 | Valen |
| 7,794,705 B2 | 9/2010 | Pecora et al. |
| 7,915,043 B2 | 3/2011 | Caligiuri et al. |
| 7,927,785 B2 | 4/2011 | Milhem et al. |
| 8,048,618 B2 | 11/2011 | Luk et al. |
| 8,088,370 B2 | 1/2012 | Pecora et al. |
| 8,343,485 B2 | 1/2013 | Pecora et al. |
| 8,425,899 B2 | 4/2013 | Pecora et al. |
| 8,637,005 B2 | 1/2014 | Pecora et al. |
| 8,709,403 B2 | 4/2014 | Pecora et al. |
| 8,956,862 B2 | 2/2015 | Pal et al. |
| 9,034,316 B2 | 5/2015 | Pecora et al. |
| 9,078,429 B2 | 7/2015 | McGann et al. |
| 9,192,695 B2 | 11/2015 | Shi |
| 9,241,959 B2 | 1/2016 | Tang |
| 9,402,377 B2 | 8/2016 | Flavell et al. |
| 9,409,906 B2 | 8/2016 | Sauvageau et al. |
| 9,499,792 B2 | 11/2016 | Chretien et al. |
| 9,504,717 B2 | 11/2016 | Strober et al. |
| 9,533,010 B2 | 1/2017 | Pecora et al. |
| 9,534,202 B2 | 1/2017 | Pecora et al. |
| 9,561,253 B2 | 2/2017 | Strober et al. |
| 9,675,643 B2 | 6/2017 | Weston et al. |
| 9,675,644 B2 | 6/2017 | Weston et al. |
| 9,687,511 B2 | 6/2017 | Weston et al. |
| 9,808,558 B2 | 11/2017 | Shi |
| 9,814,803 B2 | 11/2017 | Shi |
| 9,828,586 B2 | 11/2017 | Tom et al. |
| 9,945,854 B2 | 4/2018 | Altman et al. |
| 9,963,678 B2 | 5/2018 | Tom et al. |

(Continued)

FOREIGN PATENT DOCUMENTS

CN   107012119 A   8/2017
EP   3107995 B1   10/2019

(Continued)

OTHER PUBLICATIONS

Urso et al. "Short-Term Preservation of Mouse Bone Marrow at Refrigeration and Room Temperature for Irradiation Experiments" (1957) J App Physiol, vol. 10(2): 314-316. (Year: 1957).*

Saegeman et al. "Influence of postmordem time on the outcome of blood cultures among cadaveric tissue donors" (2009) Eur J Microbiol Infect Dis.vol. 28: 161-168. (Year: 2009).*

Brubaker et al. "Tissue recovery practices and bioburden: a systematic review" (2016) Cell Tissue Bank, vol. 17: 561-571. (Year: 2016).*

Bieback et al.: Human Alternatives to Fetal Bovine Serum for the Expansion of Mesenchymal Stromal Cells from Bone Marrow. Stem Cells. 27(9):2331-2341 (2009).

Oseni et al.: Optimization of chondrocyte isolation and characterization for large-scale cartilage tissue engineering. Journal of Surgical Research. 181:41-48 (2013).

(Continued)

*Primary Examiner* — Teresa E Knight

(74) *Attorney, Agent, or Firm* — Wilson Sonsini Goodrich & Rosati

(57) ABSTRACT

Methods are provided for extracting bone marrow cells from bone obtained from deceased donors, for preparing the bone marrow for cryopreservation and for obtaining desired cells from cryopreserved and fresh bone marrow.

19 Claims, 19 Drawing Sheets

(56) References Cited

U.S. PATENT DOCUMENTS

| | | |
|---|---|---|
| 9,974,807 B2 | 5/2018 | Strober et al. |
| 10,047,344 B2 | 8/2018 | Poon et al. |
| 10,076,113 B2 | 9/2018 | Chretien et al. |
| 10,076,542 B2 | 9/2018 | Strober et al. |
| 10,080,769 B2 | 9/2018 | Strober et al. |
| 10,143,562 B2 | 12/2018 | Malinin |
| 10,159,694 B2 | 12/2018 | Strober et al. |
| 10,183,043 B2 | 1/2019 | Strober et al. |
| 10,258,648 B2 | 4/2019 | Strober et al. |
| 10,286,112 B2 | 5/2019 | Govil |
| 10,400,218 B2 | 9/2019 | Itescu et al. |
| 10,472,608 B2 | 11/2019 | Bader et al. |
| 10,513,690 B2 | 12/2019 | Ganey et al. |
| 10,550,369 B2 | 2/2020 | Tom et al. |
| 10,603,340 B2 | 3/2020 | Strober et al. |
| 10,645,921 B2 | 5/2020 | Temple et al. |
| 10,660,329 B2 | 5/2020 | Ivanovic et al. |
| 10,660,954 B2 | 5/2020 | Mitchell et al. |
| 10,669,528 B2 | 6/2020 | Rossi et al. |
| 2002/0039786 A1 | 4/2002 | Reid et al. |
| 2002/0182186 A1 | 12/2002 | Loeb |
| 2003/0082158 A1 | 5/2003 | Symonds et al. |
| 2004/0072347 A1 | 4/2004 | Schuler et al. |
| 2004/0258670 A1 | 12/2004 | Laughlin et al. |
| 2005/0233299 A1 | 10/2005 | Sawa et al. |
| 2007/0036734 A1 | 2/2007 | Tahara et al. |
| 2007/0224587 A1 | 9/2007 | Forsell et al. |
| 2010/0178279 A1 | 7/2010 | Cunningham-Rundles et al. |
| 2010/0260721 A1 | 10/2010 | McGonagie et al. |
| 2010/0310535 A1 | 12/2010 | Nakamura et al. |
| 2010/0310536 A1 | 12/2010 | Nakamura et al. |
| 2012/0052049 A1 | 3/2012 | Woods et al. |
| 2012/0276581 A1 | 11/2012 | Arav et al. |
| 2012/0276628 A1 | 11/2012 | Khan et al. |
| 2013/0011376 A1 | 1/2013 | Peled et al. |
| 2013/0216495 A1 | 8/2013 | Motlagh et al. |
| 2013/0236433 A1 | 9/2013 | Webster |
| 2013/0302293 A1 | 11/2013 | Webster |
| 2015/0216911 A1 | 8/2015 | Vines et al. |
| 2016/0000062 A1 | 1/2016 | Chen et al. |
| 2016/0089401 A1 | 3/2016 | Woods et al. |
| 2016/0101134 A1 | 4/2016 | Tang |
| 2017/0035935 A1 | 2/2017 | Uveges et al. |
| 2017/0119819 A1 | 5/2017 | Strober et al. |
| 2017/0151287 A1 | 6/2017 | Von Maltzahn et al. |
| 2017/0198257 A1 | 7/2017 | Bader et al. |
| 2017/0239390 A1 | 8/2017 | Ganey et al. |
| 2017/0240862 A1 | 8/2017 | Ganey et al. |
| 2017/0247659 A1 | 8/2017 | Ganey et al. |
| 2018/0169301 A1 | 6/2018 | Temple et al. |
| 2018/0221410 A1 | 8/2018 | Strober et al. |
| 2018/0243337 A1 | 8/2018 | Strober et al. |
| 2018/0282762 A1 | 10/2018 | Gori |
| 2018/0326122 A1 | 11/2018 | Ganey et al. |
| 2018/0334655 A1 | 11/2018 | Ganey et al. |
| 2018/0353541 A1 | 12/2018 | Delaney |
| 2019/0000877 A1 | 1/2019 | Strober et al. |
| 2019/0083530 A1 | 3/2019 | Strober et al. |
| 2019/0091262 A1 | 3/2019 | Strober et al. |
| 2019/0151506 A1 | 5/2019 | Ganey et al. |
| 2019/0191694 A1 | 6/2019 | Temple et al. |
| 2019/0192561 A1 | 6/2019 | Strober et al. |
| 2019/0192562 A1 | 6/2019 | Strober et al. |
| 2019/0298762 A1 | 10/2019 | Strober et al. |
| 2019/0336528 A1 | 11/2019 | Strober et al. |
| 2019/0343112 A1 | 11/2019 | Woods et al. |
| 2019/0345450 A1 | 11/2019 | Radtke et al. |
| 2019/0358257 A1 | 11/2019 | Strober et al. |
| 2020/0016198 A1 | 1/2020 | Jongen et al. |
| 2020/0088718 A1 | 3/2020 | Zdanowski et al. |
| 2020/0254015 A1 | 8/2020 | Strober et al. |
| 2020/0337648 A1 | 10/2020 | Saripalli et al. |
| 2020/0399608 A1 | 12/2020 | Woods et al. |
| 2021/0214688 A1 | 7/2021 | Johnstone et al. |
| 2022/0241342 A1 | 8/2022 | Woods et al. |

FOREIGN PATENT DOCUMENTS

| | | |
|---|---|---|
| WO | WO-9307824 A1 | 4/1993 |
| WO | WO-03024215 A1 | 3/2003 |
| WO | WO-2011069117 A1 | 6/2011 |
| WO | WO-2011151452 A1 | 12/2011 |
| WO | WO-2016210292 A1 | 12/2016 |
| WO | WO-2017127755 A1 | 7/2017 |
| WO | WO-2017216775 A3 | 2/2018 |
| WO | WO-2017218948 A3 | 2/2018 |
| WO | WO-2018022651 A1 | 2/2018 |
| WO | WO-2019006328 A1 | 1/2019 |
| WO | WO-2020047236 A1 | 3/2020 |
| WO | WO-2020058324 A1 | 3/2020 |
| WO | WO-2020061180 A1 | 3/2020 |
| WO | WO-2020214400 A1 | 10/2020 |
| WO | WO-2020247341 A1 | 12/2020 |
| WO | WO-2022020210 A1 | 1/2022 |
| WO | WO-2022081909 A1 | 4/2022 |

OTHER PUBLICATIONS

Stenn et al.: Dispase, a Neutral Protease From Bacillus Polymyxa, is a Powerful Fibronectinase and Type IV Collagenase. J Invest Dermatol. 93(2):287-290 (1989).

Suire et al.: Isolation of the stromal-vascular fraction of mouse bone marrow markedly enhances the yield of clonogenic stromal progenitors. Blood. 119(11):e86-e95 (2012).

Thompson: Preparing Skeletons for Research and Teaching from Preserved Human Specimens. Thesis, pp. 1-162 (2015).

U.S. Appl. No. 17/013,379 Restriction Requirement dated Dec. 14, 2020.

U.S. Appl. No. 17/013,389 First Action Interview dated Dec. 11, 2020.

U.S. Appl. No. 17/013,400 First Action Interview dated Dec. 28, 2020.

U.S. Appl. No. 17/013,407 Office Action dated Dec. 18, 2020.

Warwick et al.: Collagenase Clostridium histolyticum: emerging practice patterns and treatment advances. Journal of Plastic Surgery and Hand Surgery. 50(5):251-326 (2016).

Aimuhem et al.: University of Cincinnati. Cryopreservation and Hyopthermal Storage of Hematopoietic Stem Cells. (2013).

Busilacchi et al.: A novel method to evaluate prethawing viability of cryopreserved CD34+ hematopoietic stem cells for autologous transplantation. The Journal of AABB. Transfusion. 60(7):1529-1535 (2020).

Donnenberg, Ph.D.: Working with Bone Marrow on a Grand Scale. McGowan Retreat. Mar. 2011.

Ferrebee et al.: The Collection, Storage and Preparation of Viable Cadaver Marrow for Intravenous Use. Blood. 14(2):140-147 (1959).

GE Healthcare Life Sciences. Cell Separation Media Reference (2014).

Han et al.: Optimization of human umbilical cord mesenchymal stem cell isolation and culture methods. Cytotechnology. 65(5):819-827 (2013).

Hibino et al.: Comparison of Human Bone Marrow Mononuclear Cells Isolation Methods for Creating Tissue-Engineered Vascular Grafts: Novel Filter System Versus Traditional Density Centrifugation Method. Tissue Engineering. Part C:17(10) (2011).

Johnstone et al.: Identification and characterization of a large source of primary mesenchymal stem cells tightly adhered to bone surfaces of human vertebral body marrow cavities. ScienceDirect. Cytotherapy. 22:617-628 (2020).

Long et al.: Accumulation of CD11b+ Gr-1+ cells in the lung, blood and bone marrow of mice infected with highly pathogenic H5N1 and H1N1 influenza viruses. Archives of Virology. 158(6):1305-1322 (2013).

Miltenyi Biotec: Isolation of Mononuclear Cells from human bone marrow aspirates by density gradient centrifugation. (2008).

U.S. Appl. No. 17/013,379 Office Action dated Feb. 18, 2021.

U.S. Appl. No. 17/013,389 Final Office Action dated Feb. 19, 2021.

U.S. Appl. No. 17/013,389 Non-Final Office Action dated Apr. 7, 2021.

(56) References Cited

OTHER PUBLICATIONS

U.S. Appl. No. 17/013,395 Final Office Action dated Mar. 12, 2021.
U.S. Appl. No. 17/013,395 Non-Final Office Action dated Apr. 13, 2021.
U.S. Appl. No. 17/013,400 Non-Final Office Action dated Apr. 13, 2021.
Walter et al.: Molecular and Functional Phenotypes of Human Bone Marrow-Derived Mesenchymal Stromal Cells Depend on Harvesting Techniques. International Journal of Molecular Sciences. 23.4382:1-12 (2020).
Fu et al.: Lymphohematopoietic graft-versus-host responses promote mixed chimerism in patients receiving intestinal transplantation. J Clin Invest . 131(8):e141698 (2021) doi: 10.1172/JCI141698.
Linch et al.: Bone marrow processing and cryopreservation. Journal of Clinical Pathology. 35(2):186-190 (1982).
PCT/US2020/025778 International Preliminary Report on Patentability dated Oct. 28, 2021.
PCT/US2021/055081 International Search Report and Written Opinion dated Jan. 20, 2021.
PCT/US2021/064152 International Search Report and Written Opinion dated Mar. 30, 2022.
U.S. Appl. No. 17/013,395 Final Office Action dated Sep. 27, 2021.
U.S. Appl. No. 17/013,400 Final Office Action dated Sep. 2, 2021.
Woods et al.: Packaging considerations for biopreservation. Transfusion Medicine and Hemotherapy 38(2):149-156 (2011).
AATB. Guidance Document, in Evaluation of Body Cooling at Standard D5.400. 2013. American Association of Tissue Banks: McLean, VA. p. 13.
Ahrens et al.: Mesenchymal stem cell content of human vertebral bone marrow. Transplantation, 2004. 78(6): p. 925-929.
Banfi et al.: Replicative aging and gene expression in long-term cultures of human bone marrow stromal cells. Tissue Eng, 2002. 8(6): p. 901-10.
Bara et al.: Concise review: Bone marrow-derived mesenchymal stem cells change phenotype following in vitro culture: implications for basic research and the clinic. Stem Cells, 2014. 32(7): p. 1713-23.
Baumert et al.: Bone marrow of multiorgan donors underutilized: implications for improvement of accessibility of hematopoietic cells for transplantations. Transplantation 93(2):165-171 (2012).
Baxter et al.: Study of telomere length reveals rapid aging of human marrow stromal cells following in vitro expansion. Stem Cells, 2004. 22(5): p. 675-82.
Bender et al.: Impact of freeze-thaw on isolation of viable CD34+ cells from human cadaveric bone marrow. The FASEB Journal. 34(S1) (2020) Abstract.
Bensidhoum et al.: Homing of in vitro expanded Stro-1- or Stro-1+ human mesenchymal stem cells into the NOD/SCID mouse and their role in supporting human CD34 cell engraftment. Blood, 2004. 103(9): p. 3313-9.
Berz et al.: Cryopreservation of hematopoietic stem cells. Am J Hematol 82(6):463-472 (2007).
Blashki et al.: Mesenchymal stem cells from cortical bone demonstrate increased clonal incidence, potency, and developmental capacity compared to their bone marrow-derived counterparts. J Tissue Eng, 2016. 7: p. 2041731416661196.
Blazar et al.: Successful donor cell engraftment in a recipient of bone marrow from a cadaveric donor. Blood 67(6):1655-1660 (1986).
Bork et al.: DNA methylation pattern changes upon long-term culture and aging of human mesenchymal stromal cells. Aging Cell, 2010. 9(1): p. 54-63.
Bruder et al.: Growth kinetics, self-renewal, and the osteogenic potential of purified human mesenchymal stem cells during extensive subcultivation and following cryopreservation. J Cell Biochem, 1997. 64(2): p. 278-94.
Chilima et al.: Designing the optimal manufacturing strategy for an adherent allogeneic cell therapy. BioProcess International, 2016. 14(9): p. 24-32 https://bioprocessintl.com/manufacturing/cell-therapies/designing-optimal-manufacturing-strategy-adherent-allogeneic-cell-therapy/.
Chinnadurai et al.: Immune dysfunctionality of replicative senescent mesenchymal stromal cells is corrected by IFNgamma priming. Blood Adv, 2017. 1(11): p. 628-643.
Choi et al.: Dissecting Cellular Heterogeneity Using Single-Cell RNA Sequencing. Mol Cells, 2019. 42(3): p. 189-199.
ClinicalTrials.gov Identifier: NCT01459107 (2011).
Co-pending U.S. Appl. No. 17/013,407, inventors Woods; Erik et al., filed on Sep. 4, 2020.
Co-pending U.S. Appl. No. 17/013,379, inventors Woods; Erik et al., filed on Sep. 4, 2020.
Co-pending U.S. Appl. No. 17/013,389, inventors Woods; Erik et al., filed on Sep. 4, 2020.
Co-pending U.S. Appl. No. 17/013,395, inventors Woods; Erik et al., filed on Sep. 4, 2020.
Co-pending U.S. Appl. No. 17/013,400, inventors Woods; Erik et al., filed on Sep. 4, 2020.
Cox et al.: High abundance of CD271(+) multipotential stromal cells (MSCs) in intramedullary cavities of long bones. Bone, 2012. 50(2): p. 510-7.
CRYO2018: The 55th Annual Meeting of The Society for Cryobiology. CSIC (2018) p. 1-2 Abstract.
CRYO2019: The 56th Annual Meeting of The Society for Cryobiology. CSIC (2019) p. 1-6 Abstracts.
Delloyd's Lab Tech. Standard sieves and Mesh sizes. Online publication. http://delloyd.50megs.com/moreinfo/mesh.html. pp. 2-3 (2018).
Dennis et al.: The STRO-1+ marrow cell population is multipotential. Cells Tissues Organs, 2002. 170(2-3): p. 73-82.
Digirolamo et al.: Propagation and senescence of human marrow stromal cells in culture: a simple colony forming assay identifies samples with the greatest potential to propagate and differentiate. Br J Haematol, 1999. 107(2): p. 275-81.
Dominici et al.: Minimal criteria for defining multipotent mesenchymal stromal cells. The International Society for Cellular Therapy position statement. Cytotherapy, 2006. 8(4): p. 315-7.
Donnenberg et al.: Clinical implementation of a procedure to prepare bone marrow cells from cadaveric vertebral bodies. Regen Med, 2011.6(6): p. 701-6.
Du et al.: Rational Design of a Fluorescent Hydrogen Peroxide Probe Based on the Umbelliferone Fluorophore. Tetrahedron Letters. 49(19):3045-3048 (2008) DOI:10.1016/j.tetlet.2008.03.063.
Dykstra et al.: Concise Review: Fat and Furious: Harnessing the Full Potential of Adipose-Derived Stromal Vascular Fraction. Stem Cells Trans! Med, 2017. 6(4): p. 1096-1108.
Eagle et al.: Assessment of an improved bone washing protocol for deceased donor human bone. Cell Tissue Bank. 16:83-90 (2014) DOI:10.1007/s10561-014-9443-z.
Eckardt et al.: Comparison of engraftment and acute GVHD in patients undergoing cryopreserved or fresh allogeneic BMT. Bone Marrow Transplant, 1993. 11(2): p. 125-31.
Ferrari et al.: Beta regression for modeling rates and proportions. J. Applied Statistics, 2004. 31(7): p. 799-815.
Flood et al.: Does practice make perfect? Part 1: The relations between hospital volume and outcomes for selected diagnostic categories. Medical Care, 1984. 22(2): p. 98-114.
Flood et al.: Does practice make perfect? Part II: The relation between volumes and other hospital characteristics. Medical Care, 1984. 22(2): p. 115-125.
Fresenius Kabi AG. 510(k) Summary. Bone Marrow Collection Stand. (2017) https://www.fda.gov/media/106490/download.
Galipeau et al.: International Society for Cellular Therapy perspective on immune functional assays for mesenchymal stromal cells as potency release criterion for advanced phase clinical trials. Cytotherapy, 2016. 18(2): p. 151-9.
Galipeau et al.: Mesenchymal Stromal Cells: Clinical Challenges and Therapeutic Opportunities. Cell Stem Cell, 2018. 22(6): p. 824-833.

(56) References Cited

OTHER PUBLICATIONS

Gorantla et al.: Development and validation of a procedure to isolate viable bone marrow cells from the vertebrae of cadaveric organ donors for composite organ grafting. Cytotherapy, 2012. 14(1): p. 104-13.

Gronthos et al.: Molecular and cellular characterisation of highly purified stromal stem cells derived from human bone marrow. J Cell Sci, 2003. 116(Pt 9): p. 1827-35.

Harrel Jr.: Regression modeling strategies with applications to linear models, logistic regression, and survival analysis. 2nd ed. Springer Series in Statistics. 2001, New York: Springer. 582.

Harrison et al.: Cell therapy-processing economics: small-scale microfactories as a stepping stone toward large-scale macrofactories. Regen Med, 2018. 13(2): p. 159-173.

Heathman et al.: Characterization of human mesenchymal stem cells from multiple donors and the implications for large scale bioprocess development. Biochemical Engineering Journal, 2016. 108: p. 14-23.

Hemacare Corporation. Isolation of Peripheral Blood Mononuclear Cells (PBMCs) Using a Density Gradient Reagent. Technical Protocol. PROT-IPBMC-V1.1 1018 (2016).

Hotta et al.: Long-term Nonhuman Primate Renal Allograft Survival Without Ongoing Immunosuppression in Recipients of Delayed Donor Bone Marrow Transplantation. Transplantation, 2018. 102(4): p. e128-e136.

Hunt. Cryopreservation of Human Stem Cells for Clinical Application: A Review. Transfus Med Hemother 38(2):107-123 (2011).

Hwang et al.: Single-cell RNA sequencing technologies and bioinformatics pipelines. Exp Mol Med, 2018. 50(8): p. 96.

Johnstone: Edit Identification and Characterization of a Large Source of Primary Mesenchymal Stem Cells Tightly Adhered to Bone Surfaces of Human Vertebral Body Marrow Cavities. ISSCR Abstract (2020).

Johnstone et al.: Identification and characterization of a large source of primary mesenchymal stem cells tightly adhered to bone surfaces of human vertebral body marrow cavities. Cytotherapy. (2020) 1-12.

Johnstone et al.: Identification and characterization of a large source of primary mesenchymal stem cells tightly adhered to bone surfaces of human vertebral body marrow cavities. Reprint https://doi.org/10.1101/2020.05.04.076950 (2020) 40 pages.

Jones et al.: Large-scale extraction and characterization of CD271+ multipotential stromal cells from trabecular bone in health and osteoarthritis: implications for bone regeneration strategies based on uncultured or minimally cultured multipotential stromal cells. Arthritis Rheum, 2010. 62(7): p. 1944-54.

Jossen et al.: Manufacturing human mesenchymal stem cells at clinical scale: process and regulatory challenges. Appl Microbiol Biotechnol, 2018. 102(9): p. 3981-3994.

Kawai et al.: Long-term results in recipients of combined HLA-mismatched kidney and bone marrow transplantation without maintenance immunosuppression. Am J Transplant, 2014. 14(7): p. 1599-611.

Kenyon et al.: Effect of depletion of class II bright cells on the immunogenicity and stem cell content of human vertebral body bone marrow. Transplant Proc 27(6):3419 (1995).

Knebel et al.: Allocation of scarce resources after a nuclear detonation: setting the context. Disaster Med Public Health Prep, 2011. 5 Suppl 1: p. S20-31.

Lechanteur et al.: Large-scale clinical expansion of mesenchymal stem cells in the GMP-compliant, closed automated Quantum(R) cell expansion system: Comparison with expansion in traditional T-flasks. Stem Cell Research & Therapy, 2014. 4(8): p. 1-11.

Li et al.: Therapeutic Delivery Specifications Identified Through Compartmental Analysis of a Mesenchymal Stromal Cell-Immune Reaction. Sci Rep, 2018. 8(1): p. 6816.

Lioznov et al.: Transportation and cryopreservation may impair haematopoietic stem cell function and engraftment of allogeneic PBSCs, but not BM. Bone Marrow Transplant, 2008. 42(2): p. 121-8.

Lipsitz et al.: A roadmap for cost-of-goods planning to guide economic production of cell therapy products. Cytotherapy, 2017. 19(12): p. 1383-1391.

Lockhart et al.: Use of Freshly Isolated Human Adipose Stromal Cells for Clinical Applications. Aesthet Surg J, 2017. 37(suppl_3): p. S4-S8.

Mendicino et al.: MSC-based product characterization for clinical trials: an FDA perspective. Cell Stem Cell, 2014. 14(2): p. 141-5.

Michalova et al.: Hematopoietic Stem Cells Survive Circulation Arrest and Reconstitute Hematopoiesis in Myeloablated Mice. Biology of Blood and Bone Marrow Transplantation. 17(9):1273-1281 (2011).

Miller et al.: Phenotypic and Functional Equivalency of Digested Bone Marrow Mesenchymal Stem Cells to Aspirated Bone Marrow Mesenchymal Stem Cells. The FASEB Journal. 33(S1) (2019) Abstract.

Mizukami et al.: Technologies for large-scale umbilical cord-derived MSC expansion: Experimental performance and cost of g000ds analysis. Biochemical Engineering Journal, 2018. 135: p. 36-48.

Moravcikova et al.: Proteomic Profiling of Native Unpassaged and Culture-Expanded Mesenchymal Stromal Cells (MSC). Cytometry A, 2018. 93(9): p. 894-904.

Morgenstern et al.: Post-thaw viability of cryopreserved peripheral blood stem cells (PBSC) does not guarantee functional activity: important implications for quality assurance of stem cell transplant programmes. Br J Haematol 174(6):942-951 (2016).

Muraglia et al.: Clonal mesenchymal progenitors from human bone marrow differentiate in vitro according to a hierarchical model. J Cell Sci, 2000. 113 ( Pt 7): p. 1161-6.

Oetjen et al.: Human bone marrow assessment by single-cell RNA sequencing, mass cytometry, and flow cytometry. JCI Insight. 3(23):7 e124928 (2018) DOI:https://doi.org/10.1172/jci.insight.124928.

Olsen et al.: Peak MSC—Are We There Yet? Front Med (Lausanne), 2018. 5: p. 178.

PCT/US2020/025778 International Search Report and Written Opinion dated Sep. 16, 2020.

Pennington et al.: Evaluation of a Sterling Cycle Controlled Rate Freezing Device for Simultaneous Cryopreservation of Multiple Units. Cryobiology. 91:146-197 (2019) Abstract.

Pereira et al.: Impact of allogeneic stem cell manufacturing decisions on cost of goods, process robustness and reimbursement. Biochemical Engineering Journal, 2018. 137: p. 132-151.

Picard et al.: Cook, Cross-validation of regression models. J . Am. Stat. Assoc, 1984. 79(428):9 pages.

Pittenger et al.: Multilineage potential of adult human mesenchymal stem cells. Science, 1999. 284(5411): p. 143-7.

Quah et al.: Monitoring lymphocyte proliferation in vitro and in vivo with the intracellular fluorescent dye carboxyfluorescein diacetate succinimidyl ester. Nat Protoc, 2007. 2(9): p. 2049-56.

Redaelli et al.: From cytogenomic to epigenomic profiles: monitoring the biologic behavior of in vitro cultured human bone marrow mesenchymal stem cells. Stem Cell Res Ther, 2012. 3(6): p. 47.

Rybka et al.: Hematopoietic progenitor cell content of vertebral body marrow used for combined solid organ and bone marrow transplantation. Transplantation, 1995. 59(6): p. 871-4.

Schneeberger et al.: Upper-extremity transplantation using a cell-based protocol to minimize immunosuppression. Ann Surg, 2013. 257(2): p. 345-51.

Schwartz et al.: Explanatory and pragmatic attitudes in therapeutical trials. J Chronic Dis, 1967. 20(8): p. 637-48.

Sherry et al.: The Influence of Warm Ischemic Time on the Viability of Deceased Organ Donor Derived Bone Marrow. The FASEB Journal. 32(S1) Abstract (2018).

Shu et al.: Development of a reliable low-cost controlled cooling rate instrument for the cryopreservation of hematopoietic stem cells. Cytotherapy 12(2):161-169 (2010).

Siclari et al.: Mesenchymal progenitors residing close to the bone surface are functionally distinct from those in the central bone marrow. Bone, 2013. 53(2): p. 575-86.

(56) References Cited

OTHER PUBLICATIONS

Simaria et al.: Allogeneic cell therapy bioprocess economics and optimization: single-use cell expansion technologies. Biotechnol Bioeng, 2014. 111(1): p. 69-83.
Simmons et al.: Identification of stromal cell precursors in human bone marrow by a novel monoclonal antibody, STRO-1. Blood, 1991. 78(1): p. 55-62.
Soderdahl et al.: Cadaveric bone marrow and spleen cells for transplantation. Bone Marrow Transplant, 1998. 21(1): p. 79-84.
Spitzer et al.: Twenty Year Follow Up of Histocompatibility Leukocyte Antigen-Matched Kidney and Bone Marrow Co-Transplantation for Multiple Myeloma with End Stage Renal Disease: Lessons Learned. Transplantation, 103(11): 2366-2372 (2019).
Squillaro et al.: Clinical Trials With Mesenchymal Stem Cells: An Update. Cell Transplant, 2016. 25(5): p. 829-48.
Stockschlader et al.: Long-term follow-up of leukaemia patients after related cryopreserved allogeneic bone marrow transplantation. British Journal of Haematology. 96:382-386 (1997).
Stockschlader et al.: Use of cryopreserved bone marrow in allogeneic bone marrow transplantation. Bone Marrow Transplant, 1995. 15(4): p. 569-72.
Stockschlader et al.: Use of cryopreserved bone marrow in unrelated allogeneic transplantation. Bone Marrow Transplant, 1996. 17(2): p. 197-9 (Abstract).
Sutherland et al.: The ISHAGE guidelines for CD34+ cell determination by flow cytometry. International Society of Hematotherapy and Graft Engineering. J Hematother, 1996. 5(3): p. 213-26.
Thomas et al.: Intravenous infusion of bone marrow in patients receiving radiation and chemotherapy. N Engl J Med 257(11):491-496 (1957).
Thompson et al.: Time and Temperature Dependent Ficoll Separation of Aged Whole Blood Neutrophils. The FASEB Journal. 33(S1) Abstract (2019).
U.S. Appl. No. 17/013,395 First Action Interview dated Dec. 1, 2020.
U.S. Appl. No. 17/013,407 Restriction Requirement dated Nov. 10, 2020.
Weinstock et al.: Radiologic and nuclear events: contingency planning for hematologists/oncologists. Blood, 2008. 111(12): p. 5440-5.
Woods et al.: Ischemia considerations for the development of an organ and tissue donor derived bone marrow bank. Journal of Translational Medicine. 18:300 (2020) 11 pages.
Woods et al.: Off the shelf cellular therapeutics: Factors to consider during cryopreservation and storage of human cells for clinical use. Cytotherapy, 2016. 18(6): p. 697-711.
Woods et al.: The learning curve and the cost of heart transplantation. Health Sery Res, 1992. 27(2): p. 219-38.
Wright, T., Factors affecting the cost of airplanes. J Aeronautical Sciences, 1936. 3(2): p. 122-128.
Wuchter et al.: Standardization of Good Manufacturing Practice-compliant production of bone marrow-derived human mesenchymal stromal cells for immunotherapeutic applications. Cytotherapy, 2014. 17(2): p. 128-39.
Yamada et al.: Overcoming memory T-cell responses for induction of delayed tolerance in nonhuman primates. Am J Transplant, 2012. 12(2): p. 330-40.
YESCOM. All Steel PEX Pipe Tube Cpvc Tubing Cutter up to 1-⅝" Hose Ratchet Style New. Publication [online], https://www.amazon.com/Steel-Tubing-Cutter-Ratchet-Style/dp/BOOLSEHSSE. p. 1 (2014).
Yusop et al.: Isolation and Characterisation of Mesenchymal Stem Cells from Rat Bone Marrow and the Endosteal Niche: A Comparative Study. Stem Cells Int, 2018. 2018: p. 6869128.
Chiang et al.: Allogeneic Mesenchymal Stem Cells in Combination with Hyaluronic Acid for the Treatment of Osteoarthritis in Rabbits. PLOS ONE. 11(2): e0149835 pp. 1-15 (2016).
U.S. Appl. No. 17/696,779 Office Action dated Jul. 18, 2022.
U.S. Appl. No. 17/013,395 Non-Final Office Action dated Jun. 17, 2022.
U.S. Appl. No. 17/199,376 Office Action dated Nov. 17, 2022.
U.S. Appl. No. 17/684,259 Final Office Action dated Sep. 30, 2022.
U.S. Appl. No. 17/684,259 Office Action dated Jun. 13, 2022.
Gorantla et al.: 2007-05-R11A Procedure for preparation of bone marrow cells from cadaveric vertebral bodies. University of Pittsburgh Medical Center, pp. 1-11 (2007).
Eurasian Application No. 202192714 Office Action dated Mar. 30, 2023.
Michalova et al.: Cadaveric bone marrow as potential source of hematopoietic stem cells for transplantation. Chimerism. 2(3):86-87 (2011).

\* cited by examiner

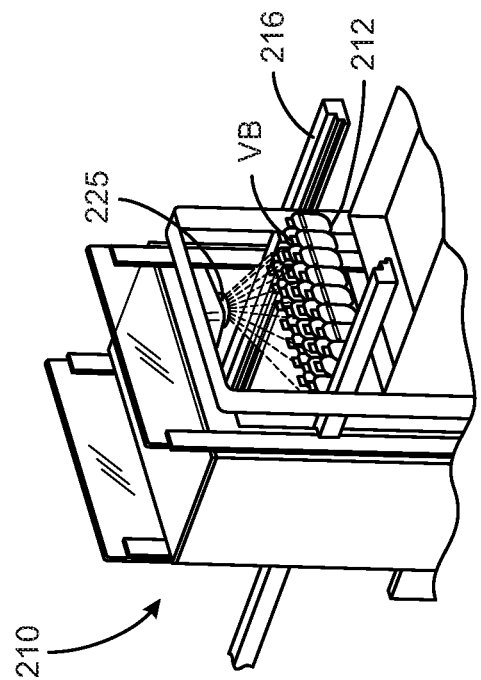
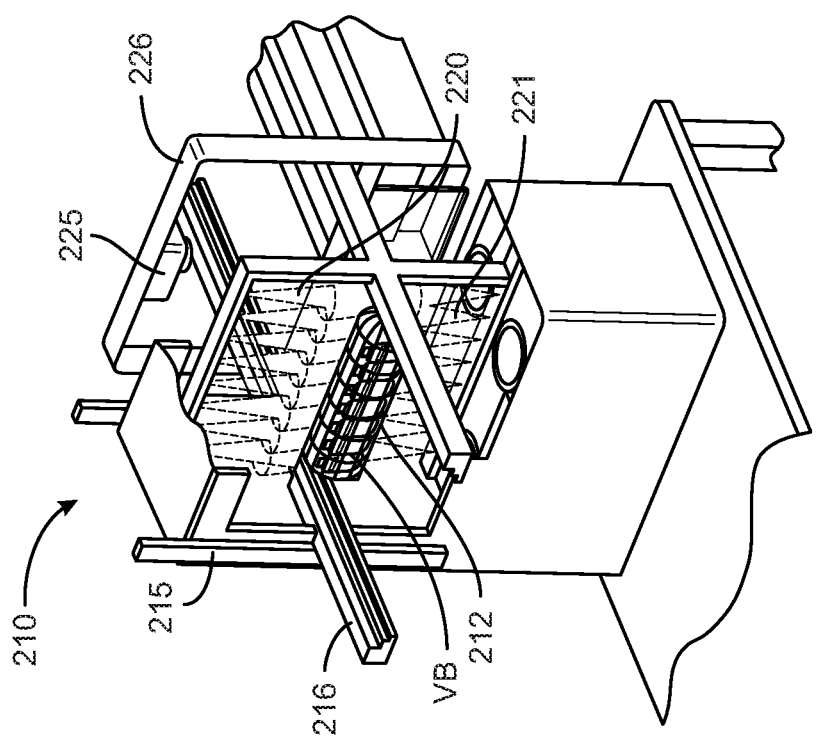
FIG. 9B
FIG. 9A

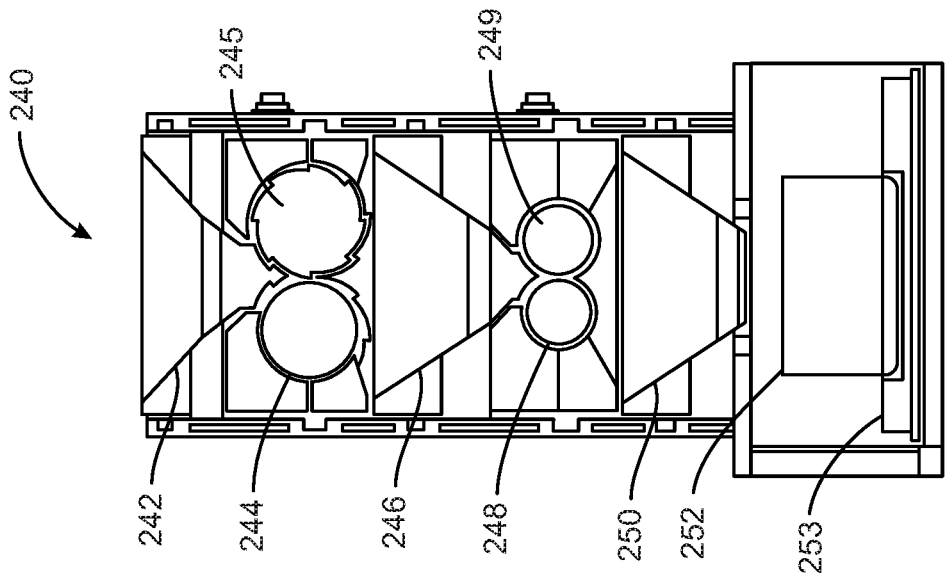
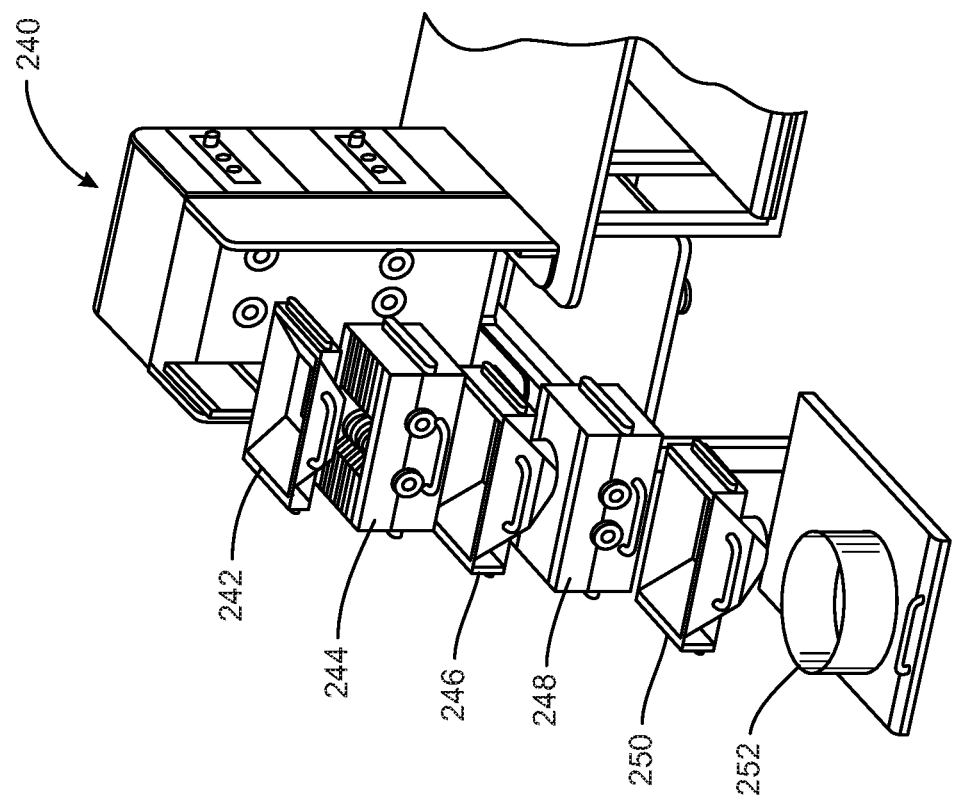
FIG. 10B
FIG. 10A

Without Body Cooling: BCT is constant = 0 hours, WIT and CIT vary from their observed minimum to maximum values.

| WIT | CIT=8.93 %Viable CD34 | Total Ischemia | CIT=18.00 %Viable CD34 | Total Ischemia | CIT=24.32 %Viable CD34 | Total Ischemia | CIT=35.84 %Viable CD34 | Total Ischemia | CIT=67.75 %Viable CD34 | Total Ischemia |
|---|---|---|---|---|---|---|---|---|---|---|
| 0.05 | 94.09% | 8.98 | 88.54% | 18.05 | 84.75% | 24.37 | 80.90% | 35.89 | 94.80% | 67.80 |
| 0.51 | 94.03% | 9.44 | 88.44% | 18.51 | 84.63% | 24.83 | 80.75% | 36.35 | 94.75% | 68.30 |
| 0.97 | 93.97% | 9.90 | 88.34% | 18.97 | 84.51% | 25.29 | 80.61% | 36.81 | 94.70% | 68.80 |
| 1.43 | 93.92% | 10.36 | 88.24% | 19.43 | 84.38% | 25.75 | 80.46% | 37.27 | 94.64% | 69.30 |
| 1.89 | 93.86% | 10.82 | 88.14% | 19.89 | 84.25% | 26.21 | 80.31% | 37.73 | 94.59% | 69.80 |
| 2.35 | 93.80% | 11.28 | 88.04% | 20.35 | 84.13% | 26.67 | 80.16% | 38.19 | 94.54% | 70.47 |
| 2.81 | 93.73% | 11.74 | 87.94% | 20.81 | 84.00% | 27.13 | 80.01% | 38.65 | | |
| 3.27 | 93.67% | 12.20 | 87.83% | 21.27 | 83.87% | 27.59 | 79.86% | 39.11 | | |
| 3.73 | 93.61% | 12.66 | 87.73% | 21.73 | 83.74% | 28.05 | 79.71% | 39.57 | | |
| 4.19 | 93.55% | 13.12 | 87.63% | 22.19 | 83.61% | 28.51 | 79.56% | 40.03 | | |
| 4.65 | 93.49% | 13.58 | 87.52% | 22.65 | 83.48% | 28.97 | 79.40% | 40.49 | | |
| 5.11 | 93.42% | 14.04 | 87.42% | 23.11 | 83.35% | 29.43 | 79.25% | 40.95 | | |
| 5.57 | 93.36% | 14.50 | 87.31% | 23.57 | 83.22% | 29.89 | 79.09% | 41.41 | | |
| 6.03 | 93.30% | 14.96 | 87.20% | 24.03 | 83.09% | 30.35 | 78.94% | 41.87 | | |
| 6.49 | 93.23% | 15.42 | 87.09% | 24.49 | 82.95% | 30.81 | 78.78% | 42.33 | | |
| 6.95 | 93.17% | 15.88 | 86.98% | 24.95 | 82.82% | 31.27 | 78.62% | 42.79 | | |
| 7.41 | 93.10% | 16.34 | 86.87% | 25.41 | 82.68% | 31.73 | 78.47% | 43.25 | | |
| 7.87 | 93.03% | 16.80 | 86.76% | 25.87 | 82.55% | 32.19 | 78.31% | 43.71 | | |
| 8.33 | 92.97% | 17.26 | 86.65% | 26.33 | 82.41% | 32.65 | 78.15% | 44.17 | | |
| 8.79 | 92.90% | 17.72 | 86.54% | 26.79 | 82.27% | 33.11 | 77.99% | 44.63 | | |
| 9.25 | 92.83% | 18.18 | 86.43% | 27.25 | 82.13% | 33.57 | 77.82% | 45.09 | | |
| 9.71 | 92.77% | 18.64 | 86.32% | 27.71 | 81.99% | 34.03 | 77.66% | 45.55 | | |
| 10.17 | 92.70% | 19.10 | 86.20% | 28.17 | 81.85% | 34.49 | 77.50% | 46.01 | | |
| 10.63 | 92.63% | 19.56 | 85.38% | 28.63 | 81.71% | 34.95 | 77.34% | 46.47 | | |
| 11.09 | 92.56% | 20.02 | 85.27% | 29.09 | 81.57% | 35.41 | 77.17% | 46.93 | | |
| 11.55 | 92.49% | 20.48 | 85.15% | 29.55 | 81.43% | 35.87 | 77.01% | 47.39 | | |
| 12.01 | 92.42% | 20.94 | 85.04% | 30.01 | 81.28% | 36.33 | 76.84% | 47.85 | | |
| 12.47 | 92.35% | 21.40 | 84.92% | 30.47 | 81.14% | 36.79 | 76.67% | 48.31 | | |
| 12.93 | 92.27% | 21.86 | 84.81% | 30.93 | 81.00% | 37.25 | 76.50% | 48.77 | | |
| 13.40 | 92.20% | 22.33 | 84.69% | 31.40 | 80.85% | 37.72 | 76.33% | 49.24 | | |

FIG. 12A

With Body Cooling: WIT is constant at its minimum = 0.05 hours, BCT and CIT vary from their observed minimum to maximum values.

| CIT | BCT=1.07 %Viable CD34 | Total Ischemia | BCT=1.62 %Viable CD34 | Total Ischemia | BCT=2.20 %Viable CD34 | Total Ischemia | BCT=3.39 %Viable CD34 | Total Ischemia | BCT=6.00 %Viable CD34 | Total Ischemia |
|---|---|---|---|---|---|---|---|---|---|---|
| 7.40 | 93.74% | 8.52 | 93.11% | 9.07 | 92.43% | 9.65 | 90.98% | 10.84 | 87.80% | 13.45 |
| 8.90 | 92.80% | 10.02 | 92.10% | 10.57 | 91.34% | 11.15 | 89.73% | 12.34 | 86.22% | 14.95 |
| 10.40 | 91.82% | 11.52 | 91.04% | 12.07 | 90.20% | 12.65 | 88.42% | 13.84 | 84.57% | 16.45 |
| 11.90 | 90.78% | 13.02 | 89.93% | 13.57 | 89.01% | 14.15 | 87.07% | 15.34 | 82.89% | 17.95 |
| 13.40 | 89.72% | 14.52 | 88.79% | 15.07 | 87.78% | 15.65 | 85.68% | 16.84 | 81.17% | 19.45 |
| 13.55 | 89.61% | 14.67 | 88.67% | 15.22 | 87.66% | 15.80 | 85.53% | 16.99 | 81.00% | 19.60 |
| 14.90 | 88.63% | 16.02 | 87.62% | 16.57 | 86.53% | 17.15 | 84.27% | 18.34 | 79.45% | 20.95 |
| 16.40 | 87.52% | 17.52 | 86.44% | 18.07 | 85.28% | 18.65 | 82.85% | 19.84 | 77.74% | 22.45 |
| 17.90 | 86.42% | 19.02 | 85.27% | 19.57 | 84.03% | 20.15 | 81.45% | 21.34 | 76.07% | 23.95 |
| 19.40 | 85.34% | 19.62 | 84.11% | 20.17 | 82.80% | 20.75 | 80.08% | 21.94 | 74.44% | 24.55 |
| 20.90 | 84.28% | 20.52 | 82.99% | 21.07 | 81.60% | 21.65 | 78.76% | 22.84 | 72.89% | 25.45 |
| 22.40 | 83.26% | 20.63 | 81.91% | 21.18 | 80.46% | 21.76 | 77.50% | 22.95 | 71.42% | 25.56 |
| 23.90 | 82.29% | 22.02 | 80.89% | 22.57 | 79.39% | 23.15 | 76.31% | 24.34 | 70.04% | 26.95 |
| 25.40 | 81.39% | 23.52 | 79.94% | 24.07 | 78.38% | 24.65 | 75.22% | 25.84 | 68.78% | 28.45 |
| 26.90 | 80.57% | 25.02 | 79.07% | 25.57 | 77.47% | 26.15 | 74.22% | 27.34 | 67.65% | 29.95 |
| 28.40 | 79.83% | 25.84 | 78.29% | 26.39 | 76.66% | 26.97 | 73.33% | 28.16 | 66.64% | 30.77 |
| 29.90 | 79.19% | 26.52 | 77.62% | 27.07 | 75.95% | 27.65 | 72.56% | 28.84 | 65.77% | 31.45 |
| 31.40 | 78.65% | 28.02 | 77.05% | 28.57 | 75.35% | 29.15 | 71.92% | 30.34 | 65.05% | 32.95 |
| 32.90 | 78.22% | 29.52 | 76.60% | 30.07 | 74.88% | 30.65 | 71.41% | 31.84 | 64.48% | 34.45 |
| 34.40 | 77.91% | 31.02 | 76.27% | 31.57 | 74.53% | 32.15 | 71.03% | 33.34 | 64.06% | 35.95 |
| 35.90 | 77.71% | 32.52 | 76.06% | 33.07 | 74.31% | 33.65 | 70.79% | 34.84 | 63.79% | 37.45 |
| 37.40 | 77.62% | 32.73 | 75.97% | 33.28 | 74.22% | 33.86 | 70.70% | 35.05 | 63.69% | 37.66 |
| 38.90 | 77.66% | 34.02 | 76.01% | 34.57 | 74.27% | 35.15 | 70.74% | 36.34 | 63.74% | 38.95 |
| 40.40 | 77.82% | 35.52 | 76.18% | 36.07 | 74.44% | 36.65 | 70.93% | 37.84 | 63.94% | 40.45 |
| 41.90 | 78.09% | 37.02 | 76.47% | 37.57 | 74.74% | 38.15 | 71.25% | 39.34 | 64.31% | 41.95 |

FIG. 12B

With Body Cooling: CIT is constant at its minimum = 7.4 hours, BCT and WIT vary from their observed minimum to observed maximum values.

| BCT | WIT=0.05 %Viable CD34 | Total Ischemia | WIT=1.95 %Viable CD34 | Total Ischemia | WIT=2.48 %Viable CD34 | Total Ischemia | WIT=3.30 %Viable CD34 | Total Ischemia | WIT=8.95 %Viable CD34 | Total Ischemia |
|---|---|---|---|---|---|---|---|---|---|---|
| 1.07 | 93.74% | 8.52 | 93.49% | 10.42 | 93.41% | 10.95 | 93.30% | 11.77 | 92.47% | 17.42 |
| 1.81 | 92.89% | 9.26 | 92.61% | 11.16 | 92.53% | 11.69 | 92.40% | 12.51 | 91.49% | 18.16 |
| 2.55 | 92.01% | 10.00 | 91.70% | 11.90 | 91.61% | 12.43 | 91.47% | 13.25 | 90.47% | 18.90 |
| 3.29 | 91.10% | 10.74 | 90.76% | 12.64 | 90.67% | 13.17 | 90.52% | 13.99 | 89.43% | 19.64 |
| 4.03 | 90.19% | 11.48 | 89.82% | 13.38 | 89.72% | 13.91 | 89.56% | 14.73 | 88.38% | 20.38 |
| 4.77 | 89.28% | 12.22 | 88.88% | 14.12 | 88.77% | 14.65 | 88.60% | 15.47 | 87.34% | 21.12 |
| 5.51 | 88.38% | 12.96 | 87.96% | 14.86 | 87.84% | 15.39 | 87.66% | 16.21 | 86.31% | 21.86 |
| 6.25 | 87.51% | 13.70 | 87.06% | 15.60 | 86.94% | 16.13 | 86.74% | 16.95 | 85.33% | 22.60 |
| 6.99 | 86.68% | 14.44 | 86.21% | 16.34 | 86.08% | 16.87 | 85.87% | 17.69 | 84.39% | 23.34 |
| 7.73 | 85.90% | 15.18 | 85.41% | 17.08 | 85.27% | 17.61 |  |  | 83.51% | 24.08 |
| 8.47 | 85.18% | 15.92 | 84.67% | 17.82 | 84.53% | 18.35 |  |  |  |  |
| 9.21 | 84.53% | 16.66 | 84.01% | 18.56 | 83.86% | 19.09 |  |  |  |  |
| 9.95 | 83.97% | 17.40 | 83.43% | 19.30 | 83.28% | 19.83 |  |  |  |  |
| 10.69 | 83.50% | 18.14 | 82.95% | 20.04 | 82.80% | 20.57 |  |  |  |  |
| 11.43 | 83.12% | 18.88 | 82.57% | 20.78 | 82.41% | 21.31 |  |  |  |  |
| 12.17 | 82.85% | 19.62 | 82.29% | 21.52 | 82.13% | 22.05 |  |  |  |  |
| 12.91 | 82.69% | 20.36 | 82.12% | 22.26 |  |  |  |  |  |  |
| 13.65 | 82.63% | 21.10 |  |  |  |  |  |  |  |  |
| 14.39 | 82.68% | 21.84 |  |  |  |  |  |  |  |  |
| 15.13 | 82.84% | 22.58 |  |  |  |  |  |  |  |  |
| 15.87 | 83.11% | 23.32 |  |  |  |  |  |  |  |  |
| 16.61 | 83.48% | 24.06 |  |  |  |  |  |  |  |  |
| 17.35 | 83.94% | 24.80 |  |  |  |  |  |  |  |  |
| 18.09 | 84.50% | 25.54 |  |  |  |  |  |  |  |  |
| 18.83 | 85.14% | 26.28 |  |  |  |  |  |  |  |  |
| 19.57 | 85.85% | 27.02 |  |  |  |  |  |  |  |  |
| 20.31 | 86.63% | 27.76 |  |  |  |  |  |  |  |  |
| 21.05 | 87.46% | 28.50 |  |  |  |  |  |  |  |  |
| 21.79 | 88.33% | 29.24 |  |  |  |  |  |  |  |  |
| 22.50 | 89.19% | 29.95 |  |  |  |  |  |  |  |  |

FIG. 12C

Without Body Cooling: BCT = 0 hours, WIT and CIT are varied from their observed minimum to maximum values.

| WIT | CIT=11.70 CFU-TOTAL | Total Ischemia | CIT=23.75 CFU-TOTAL | Total Ischemia | CIT=27.41 CFU-TOTAL | Total Ischemia | CIT=39.75 CFU-TOTAL | Total Ischemia | CIT=67.75 CFU-TOTAL | Total Ischemia |
|---|---|---|---|---|---|---|---|---|---|---|
| 1.08 | 693.630 | 12.78 | 639.001 | 24.83 | 622.416 | 28.49 | 566.465 | 40.83 | 439.527 | 68.83 |
| 1.83 | 686.798 | 13.53 | 632.170 | 25.58 | 615.585 | 29.24 | 559.634 | 41.58 | 432.696 | 69.58 |
| 2.58 | 679.967 | 14.28 | 625.339 | 26.33 | 608.754 | 29.99 | 552.803 | 42.33 | 425.865 | 70.33 |
| 3.33 | 673.136 | 15.03 | 618.507 | 27.08 | 601.922 | 30.74 | 545.972 | 43.08 | | |
| 4.08 | 666.305 | 15.78 | 611.676 | 27.83 | 595.091 | 31.49 | 539.140 | 43.83 | | |
| 4.83 | 659.474 | 16.53 | 604.845 | 28.58 | 588.260 | 32.24 | 532.309 | 44.58 | | |
| 5.58 | 652.642 | 17.28 | 598.014 | 29.33 | 581.429 | 32.99 | 525.478 | 45.33 | | |
| 6.33 | 645.811 | 18.03 | 591.183 | 30.08 | 574.598 | 33.74 | 518.647 | 46.08 | | |
| 7.08 | 638.980 | 18.78 | 584.351 | 30.83 | 567.766 | 34.49 | 511.816 | 46.83 | | |
| 7.83 | 632.149 | 19.53 | 577.520 | 31.58 | 560.935 | 35.24 | 504.984 | 47.58 | | |
| 8.58 | 625.318 | 20.28 | 570.689 | 32.33 | 554.104 | 35.99 | 498.153 | 48.33 | | |
| 9.33 | 618.486 | 21.03 | 563.858 | 33.08 | 547.273 | 36.74 | 491.322 | 49.13 | | |
| 10.08 | 611.655 | 21.78 | 557.027 | 33.83 | 540.442 | 37.49 | | | | |
| 10.83 | 604.824 | 22.53 | 550.195 | 34.58 | 533.610 | 38.24 | | | | |
| 11.58 | 597.993 | 23.28 | 543.364 | 35.33 | 526.779 | 38.99 | | | | |
| 12.33 | 591.162 | 24.03 | 536.533 | 36.08 | 519.948 | 39.74 | | | | |
| 13.40 | 581.416 | 25.10 | 526.787 | 37.15 | 510.202 | 40.81 | | | | |

FIG. 13A

With Body Cooling: WIT is constant at its minimum (0.05 hours), while BCT and CIT are varied from their observed minimum to maximum values.

| CIT | BCT=1.07 CFU-TOTAL | Total Ischemia | BCT=6.54 CFU-TOTAL | Total Ischemia | BCT=9.78 CFU-TOTAL | Total Ischemia | BCT=15.00 CFU-TOTAL | Total Ischemia | BCT=22.50 CFU-TOTAL | Total Ischemia |
|---|---|---|---|---|---|---|---|---|---|---|
| 7.40 | 624.773 | 8.52 | 248.787 | 13.99 | 123.613 | 17.23 | 74.566 | 22.45 | 333.801 | 29.95 |
| 8.90 | 617.973 | 10.02 | 241.987 | 15.49 | 116.813 | 18.73 | | | 327.001 | 31.45 |
| 10.40 | 611.173 | 11.52 | 235.187 | 16.99 | 110.012 | 20.23 | | | 320.201 | 32.95 |
| 11.90 | 604.372 | 13.02 | 228.386 | 18.49 | 103.212 | 21.73 | | | 313.400 | 34.45 |
| 13.40 | 597.572 | 14.52 | 221.586 | 19.99 | 96.412 | 23.23 | | | 306.600 | 35.95 |
| 14.90 | 590.772 | 16.02 | 214.786 | 21.49 | | | | | 299.800 | 37.45 |
| 16.40 | 583.972 | 17.52 | 207.986 | 22.99 | | | | | 293.000 | 38.95 |
| 17.90 | 577.171 | 19.02 | 201.185 | 24.49 | | | | | 286.199 | 40.45 |
| 19.40 | 570.371 | 20.52 | 194.385 | 25.99 | | | | | 279.399 | 41.95 |
| 20.90 | 563.571 | 22.02 | 187.585 | 27.49 | | | | | | |
| 22.40 | 556.771 | 23.52 | 180.785 | 28.99 | | | | | | |
| 23.90 | 549.970 | 25.02 | 173.984 | 30.49 | | | | | | |
| 25.40 | 543.170 | 26.52 | 167.184 | 31.99 | | | | | | |
| 26.90 | 536.370 | 28.02 | | | | | | | | |
| 28.40 | 529.570 | 29.52 | | | | | | | | |
| 29.90 | 522.769 | 31.02 | | | | | | | | |
| 31.40 | 515.969 | 32.52 | | | | | | | | |
| 32.90 | 509.169 | 34.02 | | | | | | | | |
| 34.40 | | | | | | | | | | |
| 35.90 | | | | | | | | | | |
| 37.40 | | | | | | | | | | |
| 38.90 | | | | | | | | | | |
| 41.03 | | | | | | | | | | |

FIG. 13B

With Body Cooling: CIT is constant at its minimum value = 7.4 hours, BCT and WIT are varied from their observed minimum to observed maximum values.

| BCT | WIT=0.05 CFU-TOTAL | Total Ischemia | WIT=1.96 CFU-TOTAL | Total Ischemia | WIT=2.48 CFU-TOTAL | Total Ischemia | WIT=3.42 CFU-TOTAL | Total Ischemia | WIT=8.95 CFU-TOTAL | Total Ischemia |
|---|---|---|---|---|---|---|---|---|---|---|
| 1.07 | 624.77 | 8.52 | 607.38 | 10.43 | 602.64 | 10.95 | 594.08 | 11.89 | 543.71 | 17.42 |
| 2.07 | 540.59 | 9.52 | 523.19 | 11.43 | 518.46 | 11.95 | | | 459.53 | 18.42 |
| 3.07 | 463.32 | 10.52 | 445.92 | 12.43 | 441.18 | 12.95 | | | 382.25 | 19.42 |
| 4.07 | 392.96 | 11.52 | 375.56 | 13.43 | 370.82 | 13.95 | | | 311.89 | 20.42 |
| 5.07 | 329.51 | 12.52 | 312.11 | 14.43 | 307.37 | 14.95 | | | 248.44 | 21.42 |
| 6.07 | 272.97 | 13.52 | 255.57 | 15.43 | 250.84 | 15.95 | | | 191.91 | 22.42 |
| 7.07 | 223.35 | 14.52 | 205.95 | 16.43 | 201.21 | 16.95 | | | | |
| 8.07 | 180.64 | 15.52 | 163.24 | 17.43 | 158.50 | 17.95 | | | | |
| 9.07 | 144.83 | 16.52 | 127.44 | 18.43 | 122.70 | 18.95 | | | | |
| 10.07 | 115.95 | 17.52 | | | | | | | | |
| 11.07 | 93.97 | 18.52 | | | | | | | | |
| 12.07 | 78.91 | 19.52 | | | | | | | | |
| 13.07 | 70.76 | 20.52 | | | | | | | | |
| 14.07 | 69.52 | 21.52 | | | | | | | | |
| 15.07 | 75.19 | 22.52 | | | | | | | | |
| 16.07 | 87.77 | 23.52 | | | | | | | | |
| 17.07 | 107.27 | 24.52 | | | | | | | | |
| 18.07 | 133.68 | 25.52 | | | | | | | | |
| 19.07 | 167.00 | 26.52 | | | | | | | | |
| 20.07 | 207.23 | 27.52 | | | | | | | | |
| 21.07 | 254.37 | 28.52 | | | | | | | | |
| 22.50 | 333.80 | 29.95 | | | | | | | | |

FIG. 13C

Without Body Cooling: BCT is constant = 0 hours, WIT and CIT are varied from their observed minimum to observed maximum values.

| WIT | CIT=11.70 CFU-GEM | Total Ischemia | CIT=23.75 CFU-GEM | Total Ischemia | CIT=27.00 CFU-GEM | Total Ischemia | CIT=40.50 CFU-GM | Total Ischemia | CIT=67.75 CFU-GM | Total Ischemia |
|---|---|---|---|---|---|---|---|---|---|---|
| 1.08 | 96.457 | 12.78 | 97.503 | 24.58 | 97.814 | 28.08 | 99.012 | 41.58 | 101.429 | 68.83 |
| 1.68 | 91.589 | 13.38 | 92.636 | 25.18 | 92.946 | 28.68 | 94.144 | 42.18 | 96.561 | 69.43 |
| 2.28 | 86.721 | 13.98 | 87.768 | 25.78 | 88.078 | 29.28 | 89.276 | 42.78 | 91.694 | 70.03 |
| 2.88 | 81.853 | 14.58 | 82.900 | 26.38 | 83.211 | 29.88 | 84.408 | 43.38 | 86.826 | 70.63 |
| 3.48 | 76.985 | 15.18 | 78.032 | 26.98 | 78.343 | 30.48 | 79.541 | 43.98 | 81.958 | 71.23 |
| 4.08 | 72.118 | 15.78 | 73.165 | 27.58 | 73.475 | 31.08 | 74.673 | 44.58 | 77.090 | 71.83 |
| 4.68 | 67.250 | 16.38 | 68.297 | 28.18 | 68.607 | 31.68 | 69.805 | 45.18 | | |
| 5.28 | 62.382 | 16.98 | 63.429 | 28.78 | 63.740 | 32.28 | 64.937 | 45.78 | | |
| 5.88 | 57.514 | 17.58 | 58.561 | 29.38 | 58.872 | 32.88 | 60.069 | 46.38 | | |
| 6.48 | 52.647 | 18.18 | 53.693 | 29.98 | 54.004 | 33.48 | 55.202 | 46.98 | | |
| 7.08 | 47.779 | 18.78 | 48.826 | 30.58 | 49.136 | 34.08 | 50.334 | 47.58 | | |
| 7.68 | 42.911 | 19.38 | 43.958 | 31.18 | 44.268 | 34.68 | 45.466 | 48.18 | | |
| 8.28 | 38.043 | 19.98 | 39.090 | 31.78 | 39.401 | 35.28 | 40.598 | 48.78 | | |
| 8.88 | 33.175 | 20.58 | 34.222 | 32.38 | 34.533 | 35.88 | 35.731 | 49.38 | | |
| 9.48 | 28.308 | 21.18 | 29.355 | 32.98 | 29.665 | 36.48 | 30.863 | 49.98 | | |
| 10.08 | 23.440 | 21.78 | 24.487 | 33.58 | 24.797 | 37.08 | 25.995 | 50.58 | | |
| 10.68 | 18.572 | 22.38 | 19.619 | 34.18 | 19.930 | 37.68 | 21.127 | 51.18 | | |
| 11.28 | 13.704 | 22.98 | 14.751 | 34.78 | 15.062 | 38.28 | 16.260 | 51.78 | | |
| 11.88 | 8.837 | 23.58 | 9.884 | 35.38 | 10.194 | 38.88 | 11.392 | 52.38 | | |
| 12.48 | 3.969 | 24.18 | 5.016 | 35.98 | 5.326 | 39.48 | 6.524 | 52.98 | | |
| 13.04 | 0.000 | 24.74 | 0.473 | 36.54 | 0.783 | 40.04 | 1.981 | 53.54 | | |

FIG. 14A

With Body Cooling: WIT is constant at its minimum value = 0.05 hours, BCT and CIT are varied from their observed minimum to observed maximum values.

| CIT | BCT=1.07 CFU-TOTAL | Total Ischemia | BCT=6.04 CFU-TOTAL | Total Ischemia | BCT=9.78 CFU-TOTAL | Total Ischemia | BCT=13.90 CFU-TOTAL | Total Ischemia | BCT=22.50 CFU-TOTAL | Total Ischemia |
|---|---|---|---|---|---|---|---|---|---|---|
| 7.40 | 98.515 | 8.52 | 71.035 | 13.49 | 50.355 | 17.23 | 27.575 | 21.35 | 0.00 | 29.95 |
| 8.40 | 98.604 | 9.52 | 71.123 | 14.49 | 50.444 | 18.23 | 27.663 | 22.35 | 0.00 | 30.95 |
| 9.40 | 98.692 | 10.52 | 71.212 | 15.49 | 50.533 | 19.23 | 27.752 | 23.35 | 0.00 | 31.95 |
| 10.40 | 98.781 | 11.52 | 71.301 | 16.49 | 50.621 | 20.23 | 27.841 | 24.35 | 0.00 | 32.95 |
| 11.40 | 98.870 | 12.52 | 71.389 | 17.49 | 50.710 | 21.23 | 27.929 | 25.35 | 0.00 | 33.95 |
| 12.40 | 98.959 | 13.52 | 71.478 | 18.49 | 50.799 | 22.23 | 28.018 | 26.35 | 0.00 | 34.95 |
| 13.40 | 99.047 | 14.52 | 71.567 | 19.49 | 50.887 | 23.23 | 28.107 | 27.35 | 0.00 | 35.95 |
| 14.40 | 99.136 | 15.52 | 71.656 | 20.49 | 50.976 | 24.23 | 28.196 | 28.35 | 0.00 | 36.95 |
| 15.40 | 99.225 | 16.52 | 71.744 | 21.49 | 51.065 | 25.23 | 28.284 | 29.35 | | |
| 16.40 | 99.314 | 17.52 | 71.833 | 22.49 | 51.154 | 26.23 | 28.373 | 30.35 | | |
| 17.40 | 99.402 | 18.52 | 71.922 | 23.49 | 51.242 | 27.23 | 28.462 | 31.35 | | |
| 18.40 | 99.491 | 19.52 | 72.010 | 24.49 | 51.331 | 28.23 | 28.550 | 32.35 | | |
| 19.40 | 99.580 | 20.52 | 72.099 | 25.49 | 51.420 | 29.23 | 28.639 | 33.35 | | |
| 20.40 | 99.668 | 21.52 | 72.188 | 26.49 | 51.508 | 30.23 | 28.728 | 34.35 | | |
| 21.40 | 99.757 | 22.52 | 72.277 | 27.49 | 51.597 | 31.23 | 28.817 | 35.35 | | |

FIG. 14B

With Body Cooling: CIT is constant at its minimum value = 7.4 hours, BCT and WIT are varied from their observed minimum to observed maximum values.

| BCT | WIT=0.05 CFU-TOTAL | Total Ischemia | WIT=0.10 CFU-TOTAL | Total Ischemia | WIT=1.54 CFU-TOTAL | Total Ischemia | WIT=1.92 CFU-TOTAL | Total Ischemia | WIT=2.49 CFU-TOTAL | Total Ischemia |
|---|---|---|---|---|---|---|---|---|---|---|
| 1.07 | 98.52 | 8.52 | 98.11 | 8.57 | 86.43 | 10.01 | 83.34 | 10.39 | 78.72 | 10.96 |
| 2.07 | 92.99 | 9.52 | 92.58 | 9.57 | 80.90 | 11.01 | 77.81 | 11.39 | 73.19 | 11.96 |
| 3.07 | 87.46 | 10.52 | 87.05 | 10.57 | 75.37 | 12.01 | 72.29 | 12.39 | 67.66 | 12.96 |
| 4.07 | 81.93 | 11.52 | 81.52 | 11.57 | 69.84 | 13.01 | 66.76 | 13.39 | 62.13 | 13.96 |
| 5.07 | 76.40 | 12.52 | 75.99 | 12.57 | 64.31 | 14.01 | 61.23 | 14.39 | 56.60 | 14.96 |
| 6.07 | 70.87 | 13.52 | 70.46 | 13.57 | 58.78 | 15.01 | 55.70 | 15.39 | 51.07 | 15.96 |
| 7.07 | 65.34 | 14.52 | 64.93 | 14.57 | 53.25 | 16.01 | 50.17 | 16.39 | 45.54 | 16.96 |
| 8.07 | 59.81 | 15.52 | 59.40 | 15.57 | 47.72 | 17.01 | 44.64 | 17.39 | 40.01 | 17.96 |
| 9.07 | 54.28 | 16.52 | 53.88 | 16.57 | 42.19 | 18.01 | 39.11 | 18.39 | 34.49 | 18.96 |
| 10.07 | 48.75 | 17.52 | 48.35 | 17.57 | 36.66 | 19.01 | 33.58 | 19.39 | 28.96 | 19.96 |
| 11.07 | 43.22 | 18.52 | 42.82 | 18.57 | 31.13 | 20.01 | 28.05 | 20.39 | | |
| 12.07 | 37.69 | 19.52 | 37.29 | 19.57 | 25.60 | 21.01 | 22.52 | 21.39 | | |
| 13.07 | 32.16 | 20.52 | 31.76 | 20.57 | 20.08 | 22.01 | 16.99 | 22.39 | | |
| 14.07 | 26.63 | 21.52 | 26.23 | 21.57 | 14.55 | 23.01 | 11.46 | 23.39 | | |
| 15.07 | 21.11 | 22.52 | 20.70 | 22.57 | 9.02 | 24.01 | 5.93 | 24.39 | | |
| 16.07 | 15.58 | 23.52 | 15.17 | 23.57 | 3.49 | 25.01 | 0.40 | 25.39 | | |
| 17.07 | 10.05 | 24.52 | 9.64 | 24.57 | 0.00 | 26.01 | 0.00 | 26.39 | | |
| 18.07 | 4.52 | 25.52 | 4.11 | 25.57 | 0.00 | 27.01 | 0.00 | 27.39 | | |
| 19.07 | 0.00 | 26.52 | 0.00 | 26.57 | 0.00 | 28.01 | 0.00 | 28.39 | | |
| 20.07 | 0.00 | 27.52 | 0.00 | 27.57 | 0.00 | 29.01 | 0.00 | 29.39 | | |
| 21.07 | 0.00 | 28.52 | 0.00 | 28.57 | 0.00 | 30.01 | | | | |
| 22.50 | 0.00 | 29.52 | 0.00 | 30.00 | 0.00 | 31.44 | | | | |

FIG. 14C

SYSTEM AND METHOD FOR EXTRACTION AND CRYOPRESERVATION OF BONE MARROW

PRIORITY CLAIM AND REFERENCE TO RELATED APPLICATIONS

This application claims priority to U.S. Provisional Application No. 62/834,087, filed on Apr. 15, 2019, and entitled "System and Method for Collecting and Preserving Bone Marrow for Clinical Use", the entire disclosure of which is expressly incorporated herein by reference. This application also claims priority to U.S. Provisional Application No. 62/938,480, filed on Nov. 21, 2019, and entitled "System and Method for Extraction and Cryopreservation of Bone Marrow", the entire disclosure of which is expressly incorporated herein by reference.

STATEMENT AS TO FEDERALLY SPONSORED RESEARCH

This invention was made with government support under AI129444, AI138334, and HL142418 awarded by the National Institutes of Health. The government has certain rights in the invention.

BACKGROUND

Bone marrow for clinical purposes is currently harvested from HLA matched siblings or optimally matched unrelated donors. Other graft sources are also now utilized including mismatched haploidentical related or unrelated donors and umbilical cord blood (CB). When transplanted into patients with certain diseases, the hematopoietic stem cells (HSCs) in the donor bone marrow engraft in the patient and reconstitute immune and hematopoietic systems.

Bone marrow is also a good source for mesenchymal stromal/stem cells (MSCs) which are self-renewing, multipotent progenitor cells with multilineage potential to differentiate into cell types of mesodermal origin, such as adipocytes, osteocytes, and chondrocytes. In addition, MSCs can migrate to sites of inflammation and exert potent immunosuppressive and anti-inflammatory effects through interactions between lymphocytes associated with both the innate and adaptive immune system.

Currently bone marrow is typically collected through a hole created in the cortical bone with a trocar needle and then using a bone marrow aspiration needle and a syringe to draw the marrow into the syringe. Multiple syringes are usually necessary to extract all of the marrow from the bone. The syringes are then removed from the sterile field and each syringe is connected to a collection bag containing anticoagulants and the marrow is pushed into the bag. This step is repeated many times, typically in both pelvic bones, and can result in contamination of the aspirate.

It was recognized sixty years ago that banked whole bone marrow (BM) from deceased donors are also a very viable source of HSCs. Recovery of highly functional BM from deceased organ donors is conceptually similar to procurement of organs and tissues that has occurred for decades, leading to more than 30,000 organ transplants and 1 million tissue transplants performed each year in the US alone. Bone marrow HSC are hardier than sensitive organs and most tissues, as these cells naturally have evolved to reside in a hypoxic environment within the BM niche and, thus, are able to withstand prolonged periods of ischemia. HSCs are typically in a quiescent (G0) state, and therefore require little metabolic substrates and produce little waste. The CD34+ HSC and progenitors within deceased organ donor BM have been found to be highly viable. Published values for viability of CD34+ cells isolated from organ donor BM (even with non-optimized and non-validated recovery and processing procedures) was 95.2%, compared to 93.5% for living donor BM. Deceased organ donors are a rich source of viable BM cells and are statistically indistinguishable from living donors by CD34+ viability and total nucleated cells (TNC). Higher yields of CD34+HSC and larger quantities of BM from organ donors allows banking of multiple BM units ($\geq 2$ units at $\sim 2\times 10^6$ CD34+ cells/kg, based on a 70 kg patient) for transplanting to multiple recipients as well as enabling certainty of being able to re-transplant in cases of primary graft failure.

Nevertheless, multiple barriers have prevented mainstream use of cadaveric bone marrow. One significant barrier has been in finding a streamlined process for controlled extraction and preservation of deceased donor bone marrow and the cell yields from that bone marrow. Current best-practice BM recovery from cadaveric organ donors involves multiple manual steps requiring several skilled operators. Typically, vertebral bodies (VB) are recovered by the transplant surgeon and initially cleaned in the OR prior to transport to the processing lab, where they are cleaned again very carefully to remove all remnants of tough connective tissue prior to further processing steps. Next the VBs are processed in groups of 3 by first manually cutting the bone into cubes and then feeding the cubes into a bone grinding system. The ground bone is then tumbled and rinsed multiple times, and cells are finally concentrated through centrifugation. Because no more than 3 VBs can be processed at one time, this procedure must be repeated three times per donor. This entirely manual current process typically requires 40 hours of total labor with almost 11 hours of processing time, at a typical cost of over $10,000 per donor.

Another concern regarding the use of cadaveric bone relates to the cryopreservation, banking and recovery of the bone. In particular, the concern relates to the quality of viable cells, such as HSCs, which can be obtained from donor bone, particularly for bones recovered at geographically dispersed locations and shipped long distances to a cryo-banking facility. Every step of the process for recovering bone from a deceased donor involves ischemia, or a shortage of oxygen to the cells in the bone marrow. It is known that variations in warm and cold ischemia time can influence the quality of HSCs and progenitor cells derived from cadaveric bone. Current tissue-banking guidelines in the US allow tissues to be recovered from deceased donors up to 24 hours following asystole, provided the body is refrigerated within 12 hours of cardiac arrest. However, body cooling is a variable that has not been investigated systematically in relation to the recovery of bone marrow. There is a need for a method for determining tolerance limits for both warm and cold ischemia which, if exceeded, would likely render the quality and functionality of recovered cells unacceptable for therapeutic use.

SUMMARY OF THE DISCLOSURE

The systems and methods disclosed herein provide a needed complement to existing bone marrow and stem cell sources. Typically, less than one-half of the patients waiting for an allo-BM transplant receive the transplant. The living donor BM registry, BM cryopreservation and autotransplantation, and umbilical cord blood banking have provided lifesaving solutions for thousands of patients with hematologic diseases; however these methods still suffer from severe limitations tied to supply and logistics and would benefit from this valuable complement. Additionally, though rare, adverse events are possible from living bone marrow donation (i.e. the risk of death associated with bone marrow donation is 1:10,000)), and while peripheral blood stem cell donation is currently much more utilized, nearly all of those donors will experience bone pain, 1 in 4 will have significant headache, nausea, or citrate toxicity, and 1/5,000 will experience splenic rupture or other fatal complication. Additionally, the long term effects of stem cell mobilizing agents are not yet known. The technical feasibility of cadaveric BM banking and donation has been demonstrated in principle, yet these vast alternative supplies are currently discarded due to issues directly addressed by this invention.

Banking BM as disclosed herein provides a ready mechanism to match many patients who cannot find a living donor. It can greatly increase post-transplant survival rates for many patients with rapidly progressing diseases and poor prognosis by allowing on-demand transplantation and reducing waiting times for these patients from many months to only 1-2 days. And importantly, this approach provides large quantities of BM from each donor, sufficient to allow engraftment of hematopoietic stem and progenitor cells (HSPCs) for several patients and enabling immediate repeat BM transplantation when needed.

The methods and systems disclosed herein enable large supplies of on-demand bone marrow for national emergency preparedness efforts. The urgent unmet need for on-demand bone marrow and stem cell transplants as a medical countermeasure for nuclear accidents or attacks has been well documented by HHS, BARDA's multi-billion dollar Project Bioshield, and the Dept. of Defense. The present disclosure also provides needed bone marrow for emerging applications such as immune tolerance induction and beyond. A protocol for processing and the actual banking of BM from organ donors for extended periods of time is critical to this approach. Additionally, patients who receive deceased donor organ transplants today could benefit from this therapy when it becomes available in the future, if BM from these donors is banked—making this method immediately beneficial to vital organ transplant recipients. If successful, other promising methods and treatments being researched have the potential to greatly enhance the value of cadaveric BM procurement and banking using the proposed method, including HLA Mismatched Unrelated Donor (mMUD) BM transplantation—making large supplies of banked bone marrow immediately usable for most recipients who need a BM transplant quickly, particularly to address severe forms of autoimmune disorders, genetic diseases, Multiple Scleroris, and Type 1 Diabetes.

In one aspect, a method is provided for obtaining bone marrow cells from deceased donor bone that comprises the steps of: obtaining a bone from a deceased donor; cleaning the bone of soft tissue; grinding the bone into bone pieces; filtering and rinsing the ground bone to produce a liquid composition; centrifuging the liquid composition of the filtered and rinsed ground bone to concentrate bone marrow cells; and extracting the bone marrow cells into a sterile container for cryopreservation and subsequent isolation of target cells.

In a further aspect, a bone cutting tool is provided for use in preparing the bone for grinding in the method described above. The bone cutting tool comprises two handles, a knife element and a ratchet and pawl mechanism for driving the knife element into the bone in which the components are connected to each other by elongated pins passing through openings in the respective components. The pins are removably retained by at least one removable retaining ring such that the bone cutting tool can be readily disassembled for cleaning and re-assembled after cleaning. The bone cutting tool is formed of medical grade stainless steel with the surfaces passivated to endure the sterilization environment.

In another aspect, a method is provided for recovering cells from deceased donor bone marrow that comprises the steps of: obtaining bone from a deceased donor; processing the bone to extract bone marrow cells from the bone; obtaining a reduced density Ficoll solution having a density of 1.063-1.052 gm/mL; introducing the reduced density Ficoll solution into a centrifuge tube to form a Ficoll gradient; layering the extracted bone marrow cells over the Ficoll gradient in the centrifuge tube; centrifuging the tubes containing the Ficoll gradient and bone marrow cells; harvesting the buffy coat cells from within the centrifuge tubes; and washing the harvested cells for subsequent use or processing.

DESCRIPTION OF THE DRAWINGS

FIGS. 9A and 9B are perspective views of a bone debriding station of the system shown in FIGS. 78A-8B.

FIGS. 10A and 10B are perspective and front views of a bone grinding station of the system shown in FIGS. 8A, 8B.

FIGS. 12A-12C are tables of CD34+ cell viability as a function of warm and cold ischemia times, without and without body cooling.

FIGS. 13A-13C are tables of CFU-Total as a function of warm and cold ischemia times, with and without body cooling.

FIGS. 14A-14C are tables of CFU-Total as a function of warm and cold ischemia times, with and without body cooling.

DETAILED DESCRIPTION

Figure 1C:
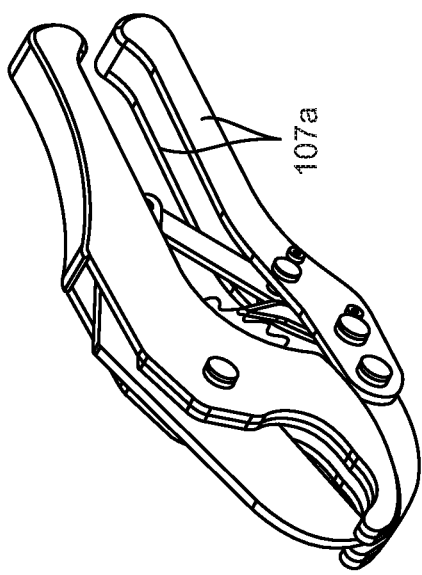
FIGS. 1A-1D are views of a hand-operated bone cutting tool according to one aspect of the present disclosure.
Figure 1A:
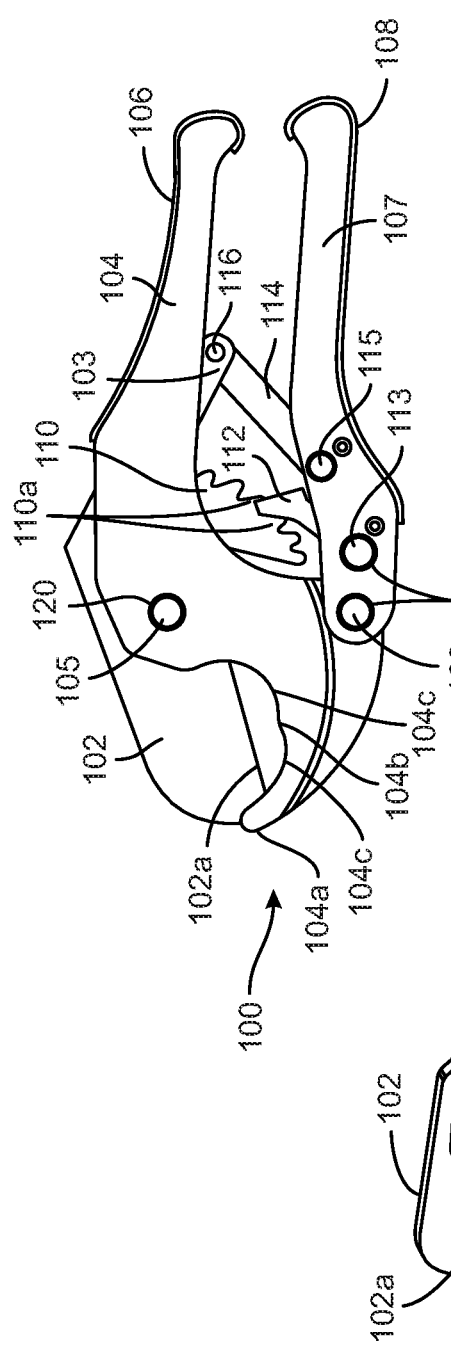

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles disclosed herein as would normally occur to one skilled in the art to which this disclosure pertains.

The present disclosure provides a clinically oriented research protocol and system that is modified to be implemented in an industrial context within state-of-the-art clean rooms. One aspect of the disclosed system involves, among other things, debridement of the incoming donor bone, initial fragmentation using a custom-made surgical stainless steel cutter, and grinding of the fragmented bone to ~3 mm fragments sizes. These refinements provide a system in which skilled tissue processing technicians can process sets of donor bones within a 6-hour window to yield meaningful quantities of viable marrow.

A first step in the process described herein is the evaluation of potential sources of deceased donor bone marrow. In processing long bones from a donor, such as the tibia, it has been found that due to conversion of red marrow to yellow with age, red marrow is limited to the ends of the long bones and varies dramatically from donor to donor. It has also been determined that mixed yellow-red marrow is poor quality, compared to wholly red marrow, such as marrow from the vertebral bodies or the ilium, and mixed yellow-red marrow contains fatty infiltrate that complicates subsequent processing steps. The best donor long bone in certain clinical experiments yielded only $1/100^{th}$ BM cells/kg compared to cells obtained from the ilia of the same donor. It has been determined, then, that long bone processing is preferably only performed in special cases, such as involving extra valuable "universal" HLA types or bone marrow with the HIV resistant delta 32 mutation.

In contrast, the vertebral body and the ilium represent the largest consistent reservoirs of high quality red marrow. Utilizing both sources has optimized the recovery of bone marrow, particularly with the implementation of the industrialized, scalable, GMP process disclosed herein. The completion of the process disclosed herein results in cryopreservation of a final product configuration of storing a 60-70 ml volume at a target of 100-150 million TNC/ml in standard blood bags, similar to the product configuration already used for cryopreserved BM for autologous transplants.

Preparing the Donor Bone

For the purposes of illustration, the donor bone is assumed to be vertebral bodies. However, it is understood that the methods described herein can be used on the ilium, a combination of the vertebral bodies and ilium, or other bones suitable for extraction of bone marrow and cells from the marrow, even donor bones with lower expected yields.

It is understood that the donor bones can be procured according to fixed protocols for clinical recovery. Bones can be recovered by surgeons or by personnel at a trained OPO (organ procurement organization) using an osteotome and mallet from consented organ and tissue donors. Unprocessed bones are preferably wrapped in sponges and towels soaked in saline to ensure moisture retention during hypothermic shipment on wet ice at a temperature of 0 to 10° F. to a processing facility.

The process for preparing the donor bone can occur soon after the bone is obtained from the deceased donor or can occur after the donor bone has been shipped in a hypothermic environment to a processing facility. Since the donor bone can experience prolonged periods of ischemia during recovery and shipment to the processing facility, care must be taken to track the length and type of ischemia—i.e., warm ischemia and cold ischemia. As described in more detail herein, bone subject to predetermined periods of warm and/or cold ischemia are suitable for obtaining meaningful quantities of viable bone marrow cells.

In the first step of processing the donor bone, the bone is debrided in an ISO-5 (class 100) environment (biosafety cabinet) with an ISO-7 (class 10,000) background (clean room), with special care taken to sterilize the bag containing the donor bone, such as by spraying with 70% isopropanol. In one embodiment, the debridement is conducted manually using scalpels, osteotomes and gouges. In processing vertebrae, typically a spinal segment including multiple vertebral levels will be provided. In a typical case, the spine segment runs from T8 to L5, for ten vertebral bodies. During initial debridement of the spinal segment, when enough soft tissue has been removed to visualize the pedicles, the pedicles are removed using either a tissue processing band saw or a bone saw, such as the Stryker System 6 Saw (Stryker, Kalamazoo, Mich.). Special care is taken to avoid breaching the cortical bone which would expose the cancellous bone, to ensure that the hypoxic cancellous bone marrow remains protected throughout the entire debriding process. The anterior element of the vertebral bodies remain, while the pedicles and posterior elements are discarded.

Using a boning knife or tissue processing band saw, the vertebral bodies are separated at the intervertebral discs. The intervertebral disc and soft tissue remaining on each vertebral body is removed with a scalpel, scissors and/or osteotomes, leaving clean, separated VBs. In the case of donor ilium, the soft tissue can be removed with gouges and a scalpel, with special care again taken to ensure that the cortical bone is not breached. Any anatomical pathologies or injuries of the bone are noted and recorded as part of the batch record for the marrow ultimately obtained from the bones. Bones damaged during the recovery process are discarded.

The VBs are placed into a sterile bag and submerged in a 10% bleach solution, yielding a concentration of 5,000 ppm free chlorine, for a predetermined period, typically 10-25 minutes. Bleach has a broad spectrum of anti-microbial activity, does not leave a toxic residue, is unaffected by water hardness and is fast acting. At the end of the period, the bones are transferred to another sterile bag and submerged in a 3% hydrogen peroxide ($H_2O_2$) solution. The bag is closed and shaken briefly to ensure that the entire surface of the bone is in contact with the solution. Most living cells include catalase, which is an enzyme that catalyzes the breakdown of $H_2O_2$ into $H_2O$ and $O_2$. This breakdown manifests as foam or froth when the $H_2O_2$ solution contacts soft tissue but not bone. The foam level can be observed as an indication of the amount of soft tissue remaining on the bone. This observation can be performed manually by a human processor or, in another embodiment, by an automated processor. The automated processor incorporates a visualization device, such as a camera, and object recognition software that can determine foam levels within the bag. The addition of an inert contrast dye can help the human or automated processor detect the foam level. If any foam or froth is observed, the bone is returned for further processing to remove all of the remaining soft tissue from the bone. Once the VBs or ilium has been cleaned of all soft tissue, the bones are transferred to a new sterile bag. The bag is filled with 1 L of PLASMA-LYTE™ (multiple electrolytes injection obtained from Baxter Healthcare, Ltd.), or other suitable sterile, nonpyrogenic isotonic solution. The bag is closed and shaken briefly to ensure that the entire bone is contacted with the PLASMA-LYTE™.

Extracting the Bone Marrow

Figure 1D:
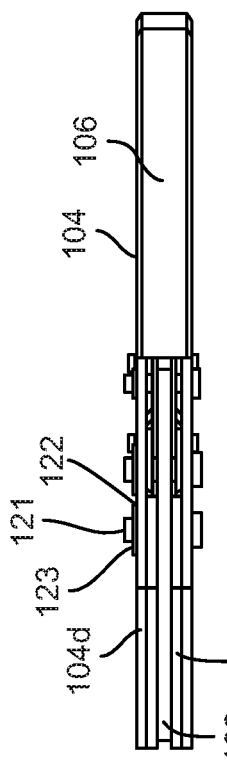
Figure 1B:
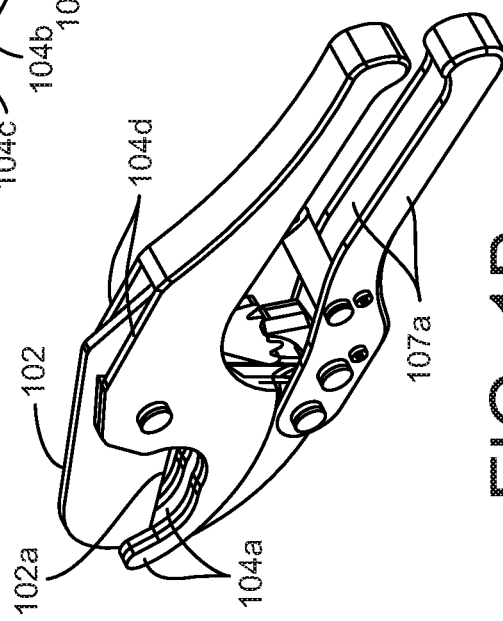

The bone is removed from the bag and from the PLASMA-LYTE™, and a sterile gauze or sponge is used to absorb any liquid remaining on the VBs. In one approach, a saw and/or anvil shears are used to cut the VBs are cut into smaller pieces, such as 1.5 cm² pieces, that are small enough for fragmenting with a bone grinder. In order to simplify the process and for increased safety to the processing personnel, a custom bone cutting tool 100 is provided as illustrated in FIGS. 1A-1D that is used to cut the VBs into the smaller pieces. The bone cutting tool 100 includes a knife element 102 with a knife edge 102a configured to penetrate and sever bone. The knife element 102 is pivotably connected at a pivot 105 to a fixed handle component 104. The fixed handle component 104 includes a jaw end 104a that is juxtaposed with the knife edge 102a to cut through a bone retained in the jaw end. As shown in FIG. 1B, the fixed handle component includes two plates 104d that are spaced apart to receive the knife component therebetween, as best seen in FIGS. 1B-1D. In particular, the knife edge 102a passes between the two plates 104d at the jaw end 104a, which ensures that the knife edge 102a passes through the bone captured by the jaw end 104a. The jaw end 104a can include two recesses 104c separated by a ridge 104b that engages the bone and helps hold the bone in the jaw end as the knife edge 102a passes through the bone. Alternatively, a single recess can be defined in the jaw end configured to retain the bone. The pivot 105 is in the form of a pin that extends through the two plates 104d and the knife component 102 sandwiched between the plates.

The bone cutting tool 100 includes a lever handle 107 that is pivotably mounted to the fixed handle 104 at a pivot 109. The pivot can include a biasing element, such as a torsion spring (not shown) configured to bias the lever handle 107 away from the fixed handle 104. The lever handle is thus configured to be pivoted toward the fixed handle when the two handles are grasped and squeezed by the user, and then to pivot away from the fixed handle when the user releases the grip on the handles. It can be appreciated that the lever handle 107 is formed of two plates 107a with the fixed handle 104 sandwiched between the two plates 107a at the pivot 109. As with the pivot 105 the pivot 109 is in the form of a pin that extends through the two plates 107a and through the fixed handle 104. Both handles 104, 107 include respective gripping plates 106, 108 that are contoured to be grasped by the palm and fingers of the user. The gripping plates 106, 108 connected the pairs of plates 104d, 107a that form the two handles. The surfaces of the gripping plates can include a non-slip feature to facilitate grasping the tool.

The lever handle 107 includes a pawl 112 that is pivotably mounted at pivot 113 to the lever handle. As with the other pivots, the pivot 113 is a pin that extends through the pair of plates 107a that form the lever handle 107 and through an end of the pawl 112. The pivot 113 includes a biasing element, such as a torsion spring (not shown), that biases the pawl 112 toward a ratchet component 110 of the knife element 102. The end of the pawl 112 is configured to engage teeth 110a on the ratchet component 110 to rotate the ratchet component, and thus the knife element 102, in a counter-clockwise direction as viewed in FIG. 1A. In particular, as the user squeezes the two handles together, the lever handle 107 moves toward the fixed handle 104 which pushes the pawl 112 upward against a tooth 110a of the ratchet to pivot the ratchet upward and counter-clockwise. When the user releases the lever handle, the handle moves away from the fixed handle, causing the pawl 112 to slide down the ratchet in the clockwise direction until it reaches another tooth 112a. Repeated squeezing of the two handles thus cases the pawl to successively rotate the ratchet. The knife element 102 also includes an integral link 103 that is pivotably connected to a free link 114 at a pivot 116. The free link 114 is pivotably connected to the lever handle 107 at a pivot 115. The integral link 103 and free link 114 hold the knife element 102 in position as the pawl traverses the ratchet component 110. The pivot 115 of the free link is a pin, like the other pivots, and includes a biasing element, such as a torsion spring (not shown) that biases the lever handle 107 away from the fixed handle 104. This allows the user to close and release the handles of the tool to successively advance the pawl 112 along the ratchet component 110, which successively advances the knife edge 102a into the bone.

In one feature of the bone cutting tool 100 of the present disclosure, the pivots 103, 109, 113 and 115 are configured to allow complete disassembly of the tool. Complete disassembly is important to allow the tool to be fully cleaned and sterilized between uses. Thus, the pivots each include a pin and retaining ring construction, with the retaining ring holding the components together on the pin. Thus, as shown in FIG. 1D, the pin 121 can extend through walls of a component, such as the opposite walls 107a of the lever handle 107 and through a corresponding bore in the component being connected, such as the knife element 102. Retaining rings 122 can engage grooves 123 at the opposite ends of the pin 121 to hold the components together. Alternatively, one end of the pin can have an enlarged head with the retaining ring engaging the opposite end of the pin. When it is necessary to clean and sterilize the tool 100, all of the retaining rings 122 can be removed, all of the pins 121 can be removed, and the connected components separated. The knife element 102, the fixed handle 104 and the lever handle 107 are thus separated so that every surface of the components can be effectively cleaned.

The elements of the bone cutting tool 100 are formed of medical grade stainless steel. The steel is preferably hardened steel capable of withstanding the forces required to cut through bone. In the cleaning process, the tool is subjected to steam sterilization, which can be deleterious to the steel. Thus, in one feature of the present disclosure, the surfaces of the stainless-steel elements are passivated to prevent oxidation of the steel elements during sterilization.

Returning to the process steps, and particularly the step of extracting bone marrow, the pieces produced by the bone cutting tool are immediately placed into a sterile pitcher and submerged in 300-500 mL of a grind media. In one aspect of the present system and method, the grind media uses PLASMA-LYTE™-A as a base with 10 U/mL heparin, 2.5% human serum albumin (HSA), and 3 U/mL Benzonase® reagent (Merck KGAA Corporation). Heparin is used as an anticoagulant. HSA provides a protein source to prevent cell adherence and adsorption to surfaces, as well as reactive oxygen scavenging. It is noted that conventional grind media utilizes DNase, but for the present disclosure Benzonase® reagent is substituted for DNase™ reagent (Qiagen Sciences LLC). Whereas DNase works only on DNA, modern pharmaceutical biotechnology processing relies on enzymes that can cleave all forms of DNA and RNA, and can reduce the viscosity of the solution in which the cells are suspended. It is noted that IMDM (Iscove's Modified Dulbecco's Media) can substitute for the PLASMA-LYTE™-A, since IMDM is suitable for rapidly proliferating high-density cell cultures and ideal for supporting T- and B-lymphocytes. It is further noted that Denarase® reagent (C-Lecta GmbH) is equivalent to Benzonase® reagent in the same quantity in the present process. Another pitcher of 300-500 mL of grind media is retained for collecting the bone fragments after grinding, and another supply of about 100 mL of the grind media is retained for rinsing through the grinder during the grinding process to prevent bone fragments from sticking to the surface of the pitcher of the grinding components.

An electric bone grinder or a purpose-built bone grinder, such as the grinder of Biorep Technologies Inc, (Miami, Fla.) can be used in an ISO-5 environment within an ISO-7 clean room. Bone types are kept separate if both VB and ilium from the same donor are being processed. The bone is kept submerged in grind media at all times during and after the grinding process. Once all of the donor bone pieces are ground, the chamber of the bone grinder is thoroughly rinsed with fresh processing media. The bone fragments are discharged from the grinder into the pitcher containing grind media.

The contents of the pitcher are transferred to sterile bags. In the next step the contents of the sterile bags are filtered to extract the solid components. In one embodiment, the contents of each bag are passed through a series of stainless steel sieves. In this embodiment, a No. 40 (425 µm) sieve is stacked on top of a No. 80 (177 µm) sieve, which is seated over a catch-pan to receive the liquid filter contents. The sterile bags containing the output from the grinder is swirled and then poured evenly over the sieve stack or filtration sets. The filtering process is observed to ensure that excessive clumping is not occurring, which can signal the presence of soft tissue or other contaminants. Bone fragments retained on the surface of the sieves are distributed evenly on the sieves and rinsed with 250 mL of fresh processing medium. In one embodiment, the processing medium used for rinsing is the grind media described above or PLASMA-LYTE™ with 2.5% HSA. The sieved bone marrow product, which can be approximately 1000 mL in a well-performed process, is transferred to sterile packs for subsequent processing and analysis. The contents of each bag are visually inspected to confirm that the contents do not include any visible bone fragments or soft tissue.

Figure 2:
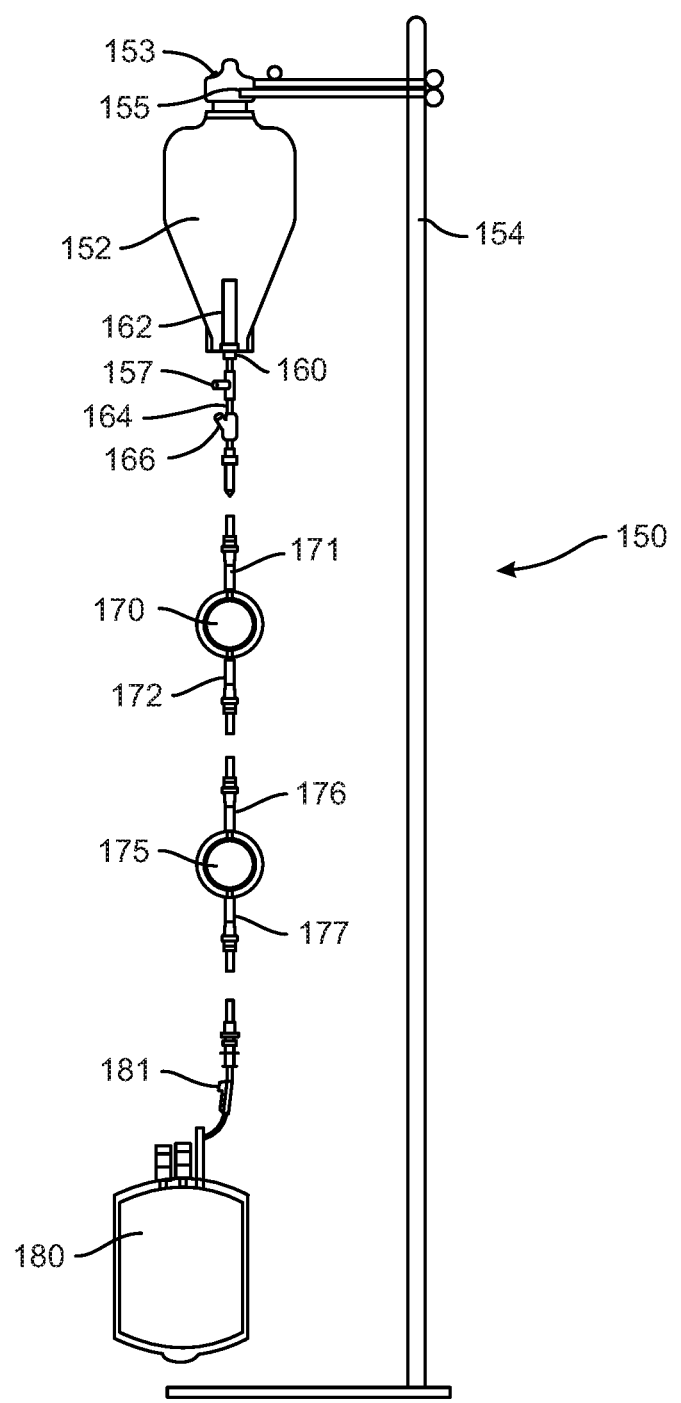
FIG. 2 is a view of a filtration system according to one feature of the present disclosure.

In another embodiment, the contents of each bag are passed through bone marrow filtration units, as depicted in FIG. 2. In this embodiment, the system 150 includes a stand 154 configured to support a sterile collection bag 152 which contains the bone fragments and media from the grinding operation described above. The stand includes a container hanger 155 configured to engage the cap 153 of the sterile bag to suspend the container. The bottom of the bag includes a discharge assembly 160 that includes a pre-filter 162 projecting into the body of the collection bag. In one specific embodiment the pre-filter 162 is an 850 µm filter. The filter 162 is connected to an output tube 164 that is connected by a container claim 166 to the input line 171 of a first in-line filter 170. In the specific embodiment, the first in-line filter is a 200 µm or a 500 µm filter. The output line 172 of the first in-line filter is connected to the input line 176 of a second in-line filter 175. The second in-line filter is a 200 µm or a 500 µm filter. The two in-line filters are initially both 500 µm for a first pass through the filter system 150. A second rinse is then performed on the grindings with the two in-line filters being 200 µm. This double-pass filtration results in a cleaner suspension and enhances removal of fat from the suspension. The second in-line filter 175 has an output line 177 that can be engaged to a sterile bag, such as bag 152 for the second filtration pass. On the second pass through the system, the output line 177 of the second in-line filter 175 can be engaged to a container clamp 181 of a transfer pack container 180. The transfer pack container can be a 600-2000 mL bag to accommodate the filtered bone marrow product, which can be approximately 1000 mL in a well-performed process.

For quality control, a small quantity of bone marrow, such as 0.3 mL, is extracted from the sterile pack 152 using a syringe at an injection site 157 and conducting inversion mixing before pulling the sample. The sample can be tested by a hematology analyzer, such as a Sysmex Hematology Analyzer, to determine the TNC (total nucleated cell) content of the sample, as an indicator of the TNC content of the bone marrow being subsequently processed.

Fat Removal and Concentration

Figure 3:
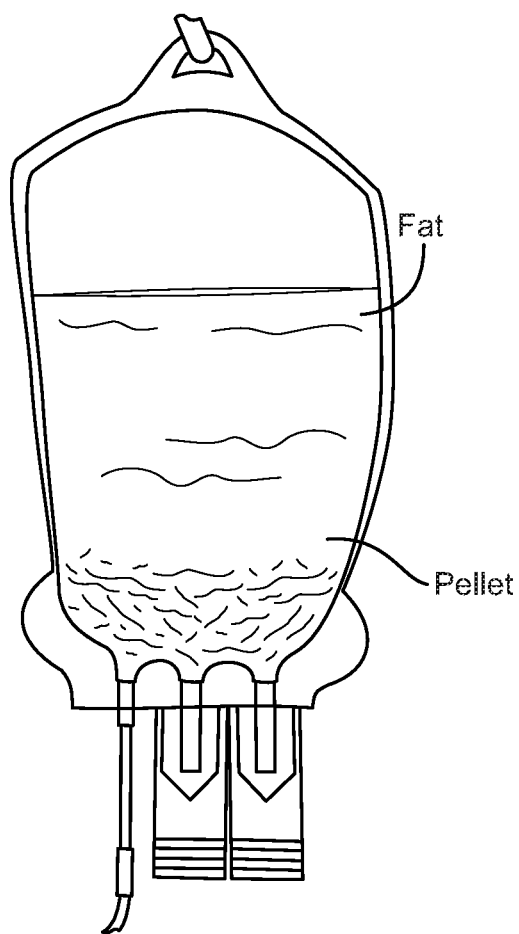
FIG. 3 is a view of a sterile bag containing a bone marrow pellet processed according to the methods of the present disclosure.
Figure 4:
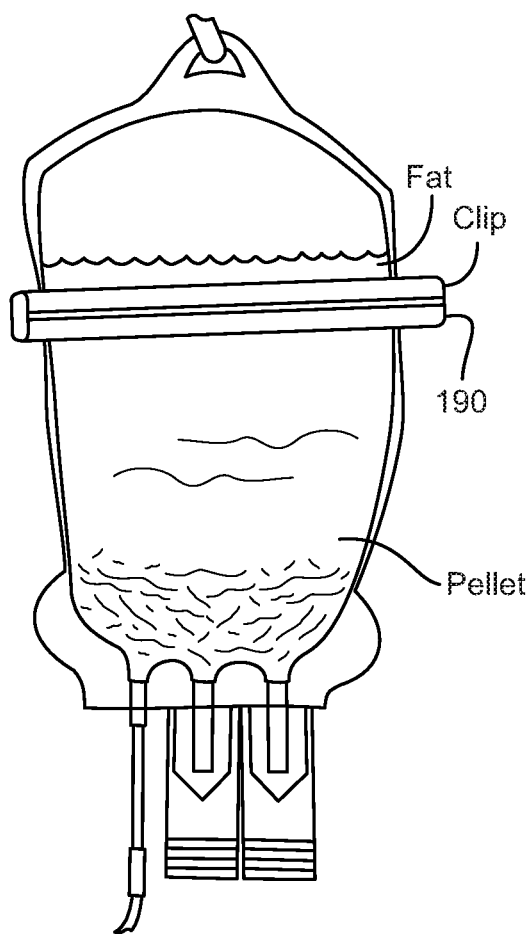
FIG. 4 is a view of the sterile bag of FIG. 3 with a clip engaging the bag to separate the fat from the bone marrow pellet.

The bone marrow product collected from the filtering step is essentially a fatty emulsion. The fat content of the suspension obtained from the sieve filtering approach disclosed above is greater than the fat content of the suspension obtained from the double-pass filtration system 150. However, in both cases, there is a need to remove the fat content from the suspension. The suspension obtained from the filtering step is recovered into 250 mL bags which are hermetically sealed with tube welders. Pairs of sterile bags and taring sticks are mounted within a centrifuge with bag ports facing down, and balanced. Volume compensating plates are used to prevent creasing of the bags during centrifugation. In one embodiment, the bags are centrifuged at 500×g for 15 minutes at room temperature to concentrate the cells, preferably to $2-3 \times 10^8$/ml. After centrifugation is complete, each bag is individually hung on a ring stand. The distinct layers within the bag are visible, with the fat layer clearly delineated on top of the supernatant with the bone marrow pellet at the bottom, as shown in FIG. 3. A new sterile bag is welded to the bag removed from the centrifuge. A bag clamp or clip 190 is placed on the bag just below the fat layer, as shown in FIG. 4, to clamp off or squeeze the bag closed beneath the fat layer. The pellet is then drained from the centrifuge bag into the new sterile bag, with the bag clip preventing passage of the fat layer. The pellet is agitated as it is drained to resuspend all of the pellet. After about half of the pellet has drained into the new bag, the tubing is closed with a hemostat or tube sealer. The second centrifuge bag is then welded to the new bag containing the pellet, and the contents of this second centrifuge bag are drained into the new bag.

Figure 5:
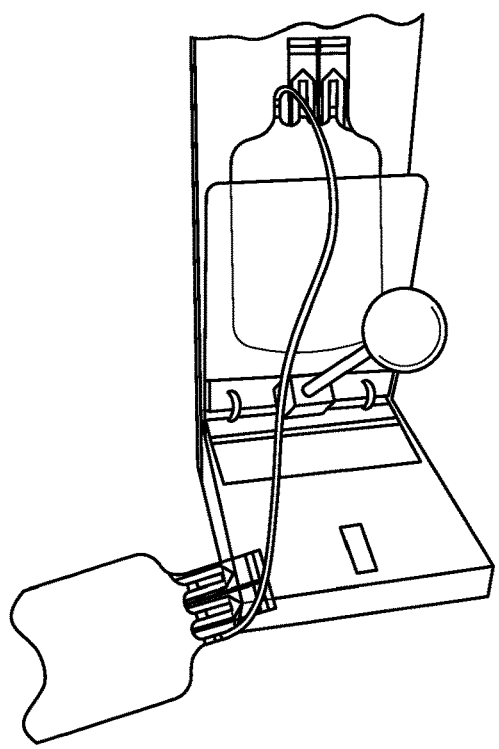
FIG. 5 shows the set-up for isolation of the bone marrow pellet

The result of this step is new sterile bags containing the bone marrow centrifuged to remove the fat. These bags of de-fatted bone marrow are then centrifuged at 500×g for 15 minutes at room temperature, with volume compensating plates to prevent creasing of the bags. Each bag is removed and suspended on a ring stand and a waste bag is welded to the bag, and a plasma extractor is used to remove the supernatant into the waste bag, as shown in FIG. 5. The tubing is clamped with a hemostat when the pellet rises or breaks. The tubing is then sealed and severed to remove the pellet—containing bag from the waste bag, which is discarded. A Luer connection is welded to the pellet-containing bag. The pellets from each bag are combined into a bulk bag using a large syringe. The pellet-containing bags are rinsed into the bulk bag using a rinse media. The bulk bag is inverted several times to ensure that all of the pellet is resuspended. A small quantity of the processed BM, such as 0.5 mL, can be removed for quality control testing for density and cell count. The test sample can also be evaluated for human leukocyte antigens, CCR5delta 32 mutation and apolipoprotein (APOE), among other things.

Cryopreservation of the Bone Marrow

It is contemplated that each bone donor can yield three or more bags of bone marrow through the process described above, based on ten vertebrae and the ilium obtained from the donor. If at the end of the process for a given donor three bags of bone marrow are not obtained, the donor can be flagged as potentially not passing overall quality control. A predetermined volume of bone marrow in each bag is contemplated, such as 70 mL contained in 250 mL bags. This predetermined volume is used to calculate the volume of freeze media components necessary for efficient cryopreservation of the bone marrow pellet. The freeze media is a solution of a rinse media and a cryopreservation composition. The cryoprotectant composition can be a permeable media, such as dimethyl sulfoxide (DMSO); 1, 2 propane diol; ethylene glycol; glycerol; foramamide; ethanediol or butane 2, 3 diol; and/or a non-permeable media, such as hydroxyethyl starch (HES), Dextran, sucrose, trehalose, lactose, raffinose, Ribotol, Mannitol or polyvinylpyrrolidone (PVP). 2.5% HSA also provides cryoprotection through oncotic pressure, cell surface protein stabilization and reactive oxygen scavenging. In a preferred embodiment, the cryopreservation media is DMSO. The rinse media can be an electrolyte medium, such as PlasmaLyte, Isolyte, IMDM or other electrolyte solutions suitable for infusion. The freeze media can also include concentrations of oxyrase to reduce oxygen content to less than atmospheric, such as to less than 3% of atmospheric concentrations. The addition of oxyrase produces a hypobaric composition that can facilitate cryopreservation.

Figure 6:
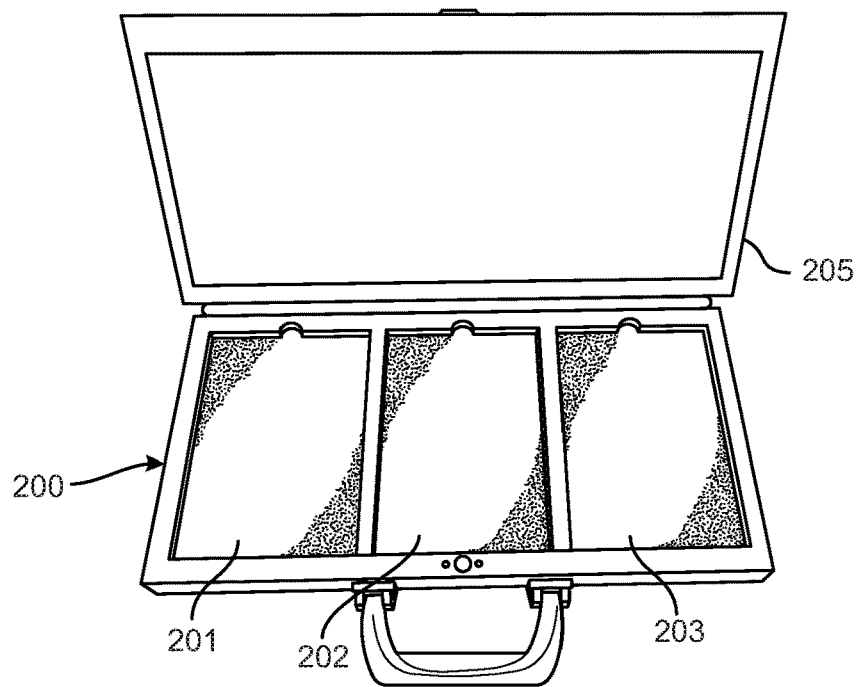
FIG. 6 is a perspective view of a cooling box according to one aspect of the present disclosure.

The freeze media is prepared by mixing the cryoprotectant and the rinse media according to the calculated total volume of freeze media needed for the volume of bone marrow collected in the prior steps. The bag containing the bone marrow is placed on a rocker for mixing and the freeze media is introduced into the bag by syringe. The freeze media is introduced at a particular rate over a predetermined time. In one embodiment, the freeze media is added at a rate of 10% of the media per minute, for a time of ten minutes. Once the media as been mixed with the concentrated bone marrow, a test sample is extracted by syringe. The remaining mixture of freeze media and bone marrow is injected in predetermined amounts into separate cryopreservation bags. In one embodiment, 70 mL of bone marrow mixture is introduced into each cryopreservation bag and air is drawn out with a syringe. At the end of the process, an 8 mL sample can be removed for sterility testing. Each cryopreservation bag is sealed to create four compartments, which are then separated for storage in cassettes to be stored in a cryofreezer. In another embodiment, the separated compartments are stored in a passive cooling box, such as cooling box 200 shown in FIG. 6.

When the test samples from the particular bone marrow batch have been validated for cell count and sterility, the bags of cryopreserved bone marrow can be further cooled for long-term storage. In one embodiment, the bags are cooled at a controlled rate to prevent damage to the bone marrow and cells. In one specific embodiment, the bags are cooled at a rate of −1 to −40° C. per minute to a temperature suitable for plunging the bags into liquid nitrogen. A suitable temperature is in the range of −40 to −100° C. Once that temperature has been reached, the bags are cooled further at a more rapid rate to a temperature of below −130° C. for storage. A cryopreservation bag is placed within a corresponding compartment 201-203 of the cooling box 200 and the overlapping cover 205 is closed over the compartments to provide a sealed environment for cryo-preservation of the contents of the bags. The cooling box is placed within a cryo freezer such that the cooling box produces a cooling rate of −0.5 to −2 C°/min, and typically of −1 C°/min, with nucleation temperatures above −20° C. The freezing process continues at the prescribed rate until the temperature of the bone marrow reaches a suitable temperature. The suitable temperature for storage of the bags is a temperature ≤−80° C. or ≤−150° C.

In another embodiment, the bags are cooled in a static chamber temperature as opposed to the controlled rate cryopreservation described above. In the passive cooling approach, the cooling box is placed in a −86° C. freezer until the bags reach a stable temperature.

It is contemplated that the cryopreservation storage can be in many forms. For instance, the cryopreserved bone marrow can be contained in bags of 1 mL to 5 mL volume or vials of 0.1 to 15 mL volumes. In a preferred embodiment, the bags with 70 mL bone marrow are stored in a cooling box within a cryogenic freezer.

The cryopreserved bone marrow is cryobanked for later thawing and extraction of desired cells. The thawed bone marrow can be provided for a wide range of treatments including treatment for leukemias, brain tumors, breast cancer, Hodgkin's disease, multiple myeloma, neuroblastoma, non-Hodgkin's lymphoma, blood cancers, ovarian cancer, sarcoma, testicular cancer, other solid organ cancer, rheumatoid arthritis, multiple sclerosis, diabetes mellitus, cystic fibrosus, Alzheimer's disease, genetic immunodeficiencies, metabolic disorders, marrow failure syndromes, and HIV. Bone marrow can also be used for induction of immunotolerance to reduce the potential rejection of an implant obtained from an organ donor. Bone marrow treatments can also be indicated for casualties caused by radiation and certain biological weapons.

Bone marrow is a well-known source for mesenchymal stromal/stem cells (MSCs) which can be harvested from previously cryo-banked organ and tissue donor bone marrow using the methods described above. MSCs are self-renewing, multipotent progenitor cells with multilineage potential to differentiate into cell types of mesodermal origin, such as adipocytes, osteocytes, and chondrocytes. In addition, MSCs can migrate to sites of inflammation and exert potent immunosuppressive and anti-inflammatory effects through interactions between lymphocytes associated with both the innate and adaptive immune system. MSCs can be used in treating osteogenesis imperfect, cartilage defects, myocardial infarction, Crohn's disease, multiple sclerosis, autoimmune disease such as Lupus, liver cirrhosis, osteo arthritis, and rheumatoid arthritis. Matched HSC/MSC units which can be used in co-transplant for treatment of graft vs. host disease (GVHD), and for hematopoietic stem cell transplant support.

Figure 7:
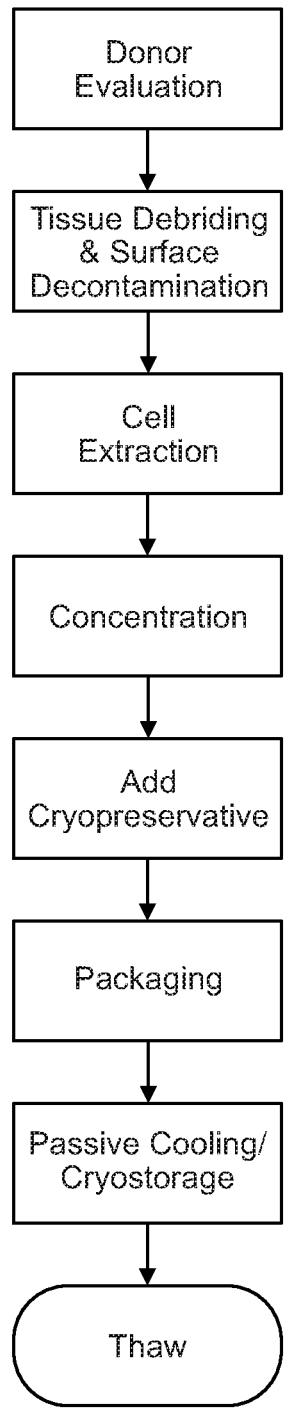
FIG. 7 is a flowchart of the steps of one method according to the present disclosure

The present method provides a system for extracting and banking bone marrow for future clinical use according to the process steps described above, as summarized in the flowchart of FIG. 7. This method can eliminate the failures of the current methods of matching bone marrow donors to groups that are tough to match, such as certain minorities. Once the bone marrow is cryopreserved and banked there is no uncertainty as to the source of the bone marrow, there is no wait for a future recipient and the bone marrow is available in large repeatable volumes.

Automated System for Recovery of Bone Marrow

The present disclosure contemplates an automated process for recovery of the bone marrow, and even selection of cells from the bone marrow. In one aspect, an automated system 209 includes sequential stations, as depicted in FIGS.

8A-8B. The first station 210 of the automated process debrides the VBs to remove all soft tissue. In contrast to the manual process that operates on one VB at a time, the automated process is configured to debride an entire donor VB set (which can be at least ten vertebral bodies). The VBs are mounted on a rack or tray 212 that is configured to support the vertebral body set from a given donor. The tray 212 is placed on transfer rails 216 of a housing 215, as shown in FIGS. 9A-9B, with the tray advanced automatically or manually into the interior of the housing. The housing 215 supports a plurality of hydrojets 220 that direct high pressure and high velocity jets of saline onto the VBs. In the known manual process, a manual hydrojet, operating at lower velocities and pressures, directs a stream of detergent onto the VB. In the manual process, the detergent is needed to clean the VBs of the soft tissue. In contrast, the automated cleaning station 210 of the present disclosure uses a saline medium, with the velocity and pressure of the water jets being sufficient to dislodge all soft tissue from the VBs. The automated cleaning station of the present disclosure includes jets configured to produce a direct stream or narrow "V" water/saline jet that generates a high concentrated impact force at varying distances. To achieve good coverage of the VBs, the device includes many direct jets at close spacing at different orientations relative to the VBs, which allows for uniform cleaning independent of position of the VB in the device. In the illustrated embodiment of FIG. 9A, the hydrojets are provided in an upper 220 and a lower row 221. The "V" jets are aligned at different angles to achieve full coverage of the surfaces of the VBs. In addition, or alternatively, the hydrojets 220, 221 can be configured to oscillate over the tray of VBs to ensure complete coverage.

A visualization device 225 is arranged at the outlet of the debridement station 210 that is operable to visualize and interpret the VBs exiting the station to determine if all of the soft tissue has been removed, as shown in FIG. 9B. If not, then the VBs are returned along the rails 216 back into the housing for further hydrojet processing. It is contemplated that a controller (not shown) can be provided to control the movement of the tray 212 along the rails 216 and to interpret the signals generated by the visualization device 225. The visualization device can include a camera that obtains an image of the VBs and the controller can include imaging software capable of recognizing the soft tissue in the acquired image. A dye can be applied to the cleaned VBs at the end of the hydrojet debridement process, in which the dye is absorbed by soft tissue but not bone. The dye can thus provide contrast to facilitate differentiation of any remaining soft tissue from the bone. The visualization device 225 can be configured to pan across the VBs, such as by translating along a frame 226 and by translating the frame in order to view the VBs at all angles.

Figure 8A:
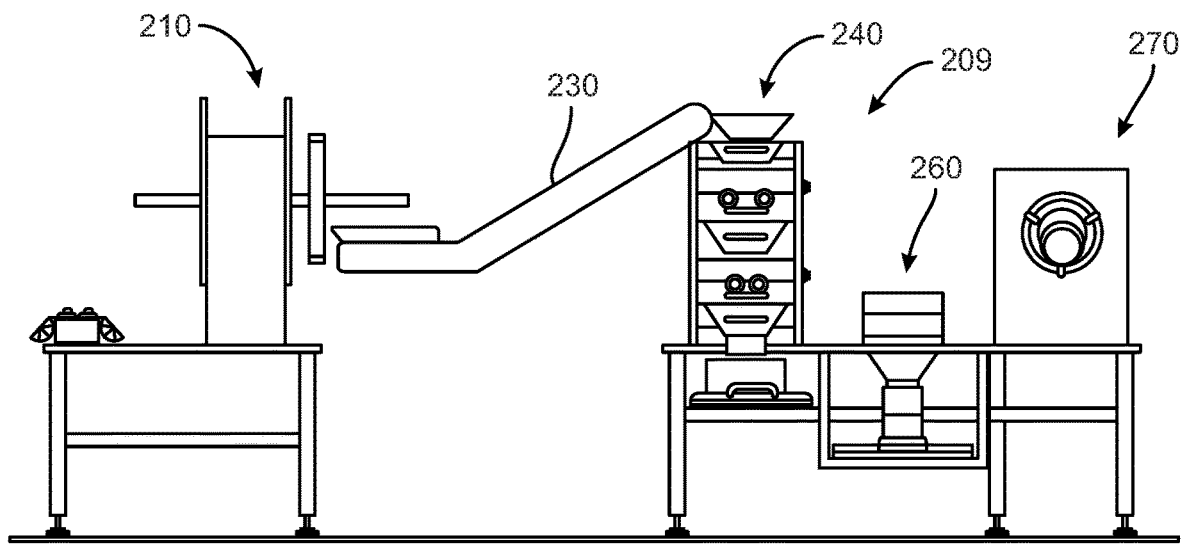
FIGS. 8A and 8B are side and perspective views of an automated bone processing system according to one aspect of the present disclosure.
Figure 8B:
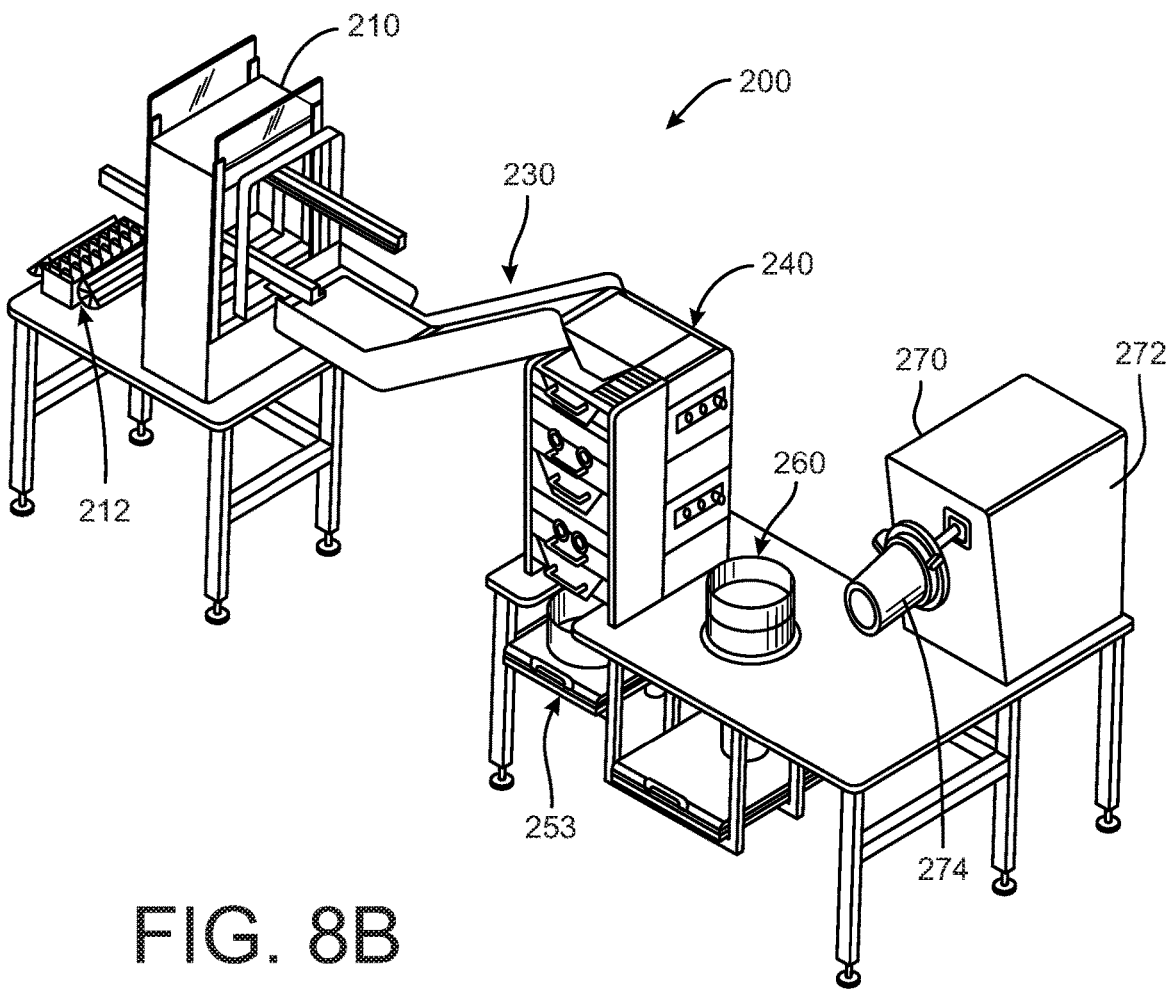

Returning to FIGS. 8A-8B, once it is determined that the VBs are cleaned of all soft tissue, the debrided VBs are then fed by a conveyor 230 to an automated grinding station 240 to produce appropriately sized pieces for tumbling and final cell extraction. The manual "cubing" process described above can be variable, time consuming, and potentially not safe for the operator. The automated system includes a grinding station that combines the steps of "cubing" the VBs (i.e., cutting the VBs into small pieces) and grinding the cubed VBs to reduce the VBs to 2-3 mm pieces. The rails 216 and tray 212 can be configured to deposit the debrided VBs onto the conveyor 230 which then automatically transfers the VBs to an input hopper 242 of the grinding station 240, shown in more detail in FIGS. 10A-10B. The VBs are directed through an initial mill cutter module 244, then through a funnel 246 to a fine mill cutter module 248, as shown in FIG. 10A. As shown in FIG. 10B the initial mill cutter module 242 includes opposed rotating grinding mills 245 that are separated by a predetermined gap, such as a 5-8 mm gap, so that the incoming VBs are ground into coarse-sized segments. The coarse ground segments are fed to the fine mill cutter module 248 in which smaller diameter grinding mills 249 are provided. The fine grind mills 249 are separated by a smaller gap, on the order of 2-3 mm, to produce finely ground VB segments. As shown in FIG. 10A, a funnel 246 conveys the coarse ground segments to the second grinding mill 248, and a funnel 250 directs the finely ground VB segments to a collection pan 252 supported on a plate 253. During the milling operation, a measured volume of processing/resuspension medium with DNAse can be directed through the upper hopper, onto grinding cutters. This medium can be manually introduced during the operation of the grinding station 240, or can be automatically implemented through nozzles incorporated into the hopper 242.

Figure 11:
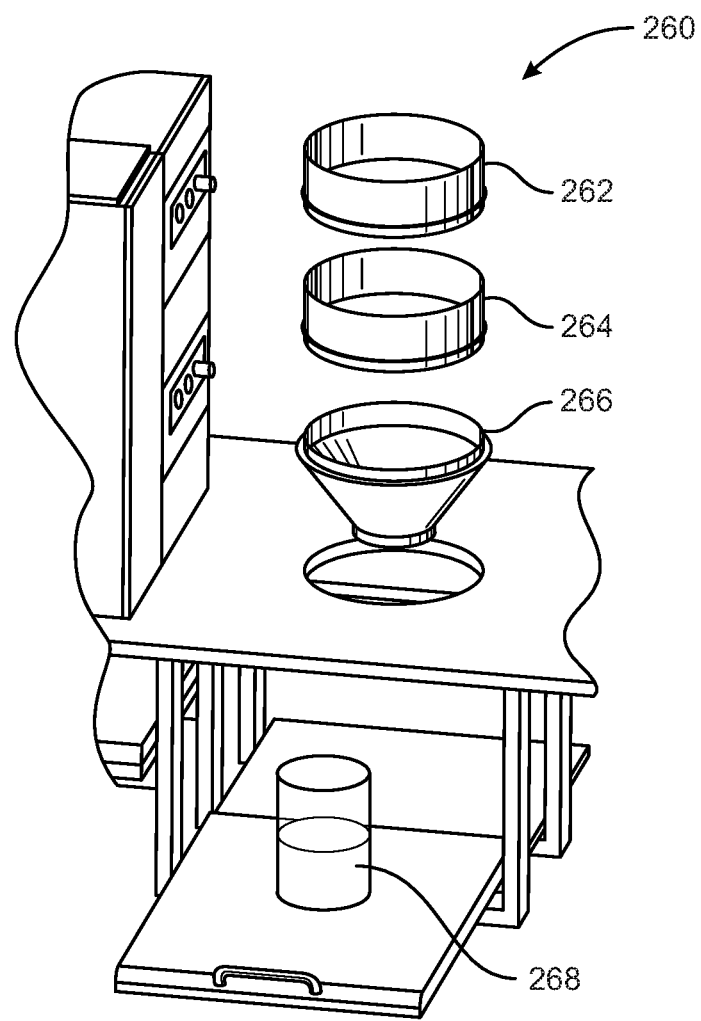
FIG. 11 is a perspective view of a sieve station of the system shown in FIGS. 8A, 8B.

The finely ground VB segments and processing medium are collected in the collection pan 252 and the plate 253 can be moved to a sieve station 260 (FIGS. 8A-8B), whether manually or automatically. Once at the sieve station 260 the contents of the pan 252 are dropped into a sieve cartridge unit which includes two 12" diameter filter sieves-a #40 sieve 262 on top followed by a finer #80 sieve 264, as depicted in FIG. 11. A funnel 266 directs the filtered contents to a collection container 268. The grindings retained by the filters are rinsed within the sieve station 260 with processing/resuspension medium that does not include DNAse. The liquid bone marrow product in the collection container 268 can be analyzed to determine cell content and then concentrated and packaged in appropriate volumes for cryopreservation, as described below. Alternatively, some or all of the processed bone marrow can be further processed using automated cell selection approaches for specialized cell products such as CD34+ cells. Because large volumes of cells can be recovered from a single organ donor with this approach, one donor could yield multiple product types. Moreover, since the source is primary bone marrow (as opposed to G-CSF mobilized peripheral blood) the cell product will endure cryopreservation processing.

In one modification, the output from the grinding station 240 or the sieve station 260 can be automatically fed to a collection bag for cryogenic treatment. In this modification, the lower funnel 250 can be configured to direct the contents to a fluid line connected to a sterile bag. A peristaltic pump can engage the fluid line to pump the output from the grinding station to the sterile bag. A similar arrangement can be engaged to the funnel 266 of the sieve station.

The content of the collection container 268, which is essentially a bone marrow slurry, is conveyed, either manually or automatically, to an adjacent tumbler station 270 that includes a mechanical tumbler 272 and a large disposable vessel 274 that can contain the entire contents of ten processed VBs and associated processing/resuspension medium. The tumbler 272 has a paddle for agitation of the grinding slurry to mechanically liberate cells. When the tumbling cycle is complete, the contents of the tumbler are poured through a sieve magazine into the vessel 274. The contents of the vessel 274 can be processed further or prepared for cryogenic storage.

Cell Isolation from Bone Marrow

In one aspect of the present disclosure, a method is provided for selecting CD34− expressing (CD34+) cells from deceased donor bone marrow using density reduced Ficoll and an immunomagnetic CD34+ cell isolation kit. Surprisingly, it has been found that cell isolation using density reduced Ficoll prior to CD34 selection is beneficial to obtain high purity and viability CD45/CD34+ cells from freshly prepared deceased donor bone marrow. On the other hand, Ficoll at conventional density has been found to be optimal for CD45/CD34+ cell selection from thawed cryopreserved deceased donor bone marrow.

Vertebral sections obtained from a recently deceased donor were processed as described above. Thus, in one embodiment, the bone is cleaned of all soft tissue and then cut into small pieces that were immediately submerged into 500 mL of grinding media. The grinding media can be PLASMA-LYTE™ A injection pH 7.4, multiple electrolytes, injection type 1 USP (PLASMA-LYTE™) containing 2.5% human serum albumin (HSA), 3 U/ml denarase, and 10 U/ml heparin. The sectioned VB are ground using a bone grinder, filtered and rinsed with rinse media (such as PLASMA-LYTE™ with 2.5% HSA). The entire cell suspension is centrifuged to concentrate cells to $2-3\times10^8$/ml and the cell concentration is extracted. A portion or all of the resulting BM preparation can be used immediately for CD34 selection, while the remainder can be prepared for cryopreservation. The cryopreserved portion involves adding a final concentration of 10% DMSO and 5% HSA to the BM cells and bringing the preparation to $-86°$ C., either by passive cooling or by controlled cooling at a rate of approximately $-1°$ C./min, after which the cryopreserved portion is plunged into liquid nitrogen.

For selection of CD34+ cells, either the newly processed BM preparation is used or a previously cryopreserved portion is thawed for use. Ficoll-Paque PLUS is added to the BM preparation to separate the desired CD34+ cell component of the bone marrow. It has been found for cell selection from cryopreserved bone marrow that the conventional density for the Ficoll of 1.077 g/mL produces acceptable results. However, in one aspect of the present disclosure, for cell selection from freshly prepared deceased donor bone marrow the Ficoll density is reduced from the conventional density. In particular, the density is reduced by mixing Ficoll-Paque PLUS (density 1.077 g/mL, GE Company) with Plasma Lyte-A Injection pH 7.4 (Baxter Healthcare 2B2544X) in specific proportions to obtain an overall density of less than 1.077 g/ml, particularly 1.063-1.052 g/mL. In one specific embodiment, the density of 1.063 g/mL was found to be optimal for isolation of CD34+ cells, taking into account quantity, viability and purity of the CD34+ cells.

In one embodiment, 5 ml of the 1.063 g/mL density Ficoll solutions is pipetted into 15-ml centrifuge tubes, and the BM solution generated from VBs of deceased donors is carefully layered over the Ficoll gradient. The tubes are centrifuged for 30 min at 400 g without break at room temperature. After centrifugation, buffy coat cells are harvested carefully, and the cells are washed in phosphate-buffered saline (PBS) containing 0.5% HSA and 2 mM Ethylenediaminetetraacetic acid (EDTA) (MACS buffer, Miltenyi). In one specific embodiment, centrifugation is performed for 5 min at 400 g, and the resulting cell pellets are resuspended in 10 ml PBS, followed by a second centrifugation for 5 min at 400 g.

Nucleated cells in the isolated buffy coat can be counted using a Sysmex XP-300. A Cellometer Vision (Nexcellom) or flow cytometer can be used to determine cell counts of purified CD34 cells. 20 microliters of AOPI can be added to 20 microliters of cells and after mixing total viable cells can be determined. The CD34+ cells can be selected by a positive immune separation method using a CliniMAX system (Miltenyi, Bergisch Gladbach, Germany) or an Easy-Sep CD34 kit (Stemcell Technologies, Vancouver, BC, Canada) in accordance with the protocol of the manufacturer. From testing at various Ficoll densities it has been surprisingly determined that the lower Ficoll density contemplated in the present disclosure (i.e., 1.063-1.052 gm/mL vs. the conventional 1.077 gm/mL density) leads to more optimum cell recovery. Optimization is based on purity, viability and yield of selected CD34 cells. A target of >90% purity and >90% viable CD34+ cells is preferred. While lower Ficoll densities resulted in greater purity and fewer dead cells, it was surprisingly found that a greater portion of the CD34+ cells present in the deceased donor whole bone marrow before selection are lost using the lower Ficoll densities to prepare buffy coat. Thus, the high viability and purity of CD45/CD34+ cells achieved at the conventional Ficoll density gradient also leads to a large loss in yield (approximately 60% loss of input CD34+ cells).

Thus, in accordance with one aspect of the present disclosure, for freshly prepared the optimal density of Ficoll for selection of CD45/CD34+ cells at >90% purity and viability is less than 1.077 and particularly 1.063-1.052. This Ficoll density provides a higher yield of CD45/CD34+ cells with similar purity and cell viability to the conventional Ficoll density approach.

In another aspect of the present disclosure, the CD34+ cells can be initially acquired from a freshly prepared deceased donor bone marrow using the reduced density Ficoll-Paque described above. The BM can be cryogenically frozen and then the CD34+ cells can be acquired later using conventional density Ficoll-Paque. This approach essentially allows selective recovery of cells from deceased donor bone marrow—either before freezing using the modified Ficoll density or after freezing and thawing using conventional Ficoll density.

Recovery of MSCs from Processed Bone Marrow

In another feature of the systems and methods disclosed herein, a method is provided for recovering mesenchymal stem cells (MSCs) from enzymatically digested vertebral body (VB) bone fragments that are the byproduct of the VB grinding and elution steps of the methods described herein. In this method, a mixture of both collagenase and neutral protease is used to obtain the highest possible yields of vertebral bone adherent MSC (vBA-MSC). The MSCs can be recovered from cryopreserved VB bone fragments that are later processed according to the present disclosure. In one specific aspect, recombinant *Clostridium histolyticum* collagenase, comprised of the two active isoforms, is used in effective amounts in the MSC extraction process. The mixture of cells liberated by digesting VB bone fragment is cultured on tissue-coated plastic in the presence of Mesencult medium to select proliferative vBA-MSC. Freshly digested preparations as well as different passages of VB-MSC can be characterized by flow cytometry, colony forming unit-fibroblast (CFU-F) potential, population doubling time (PDT) and trilineage (adipogenic, chondrogenic and osteogenic) differentiation in vitro.

The present disclosure thus contemplates a method for optimizing digestion and MSC recovery from vertebral bone fragments using a combination of purified collagenase and neutral protease. In one specific embodiment, the collagenase is DE collagenase (Vitacyte), which is comprised of purified *Clostridium histolyticum* collagenase and *Paneibacillus polymyxa* neutral protease. In accordance with one aspect of the disclosure, optimal neutral protease concentration and collagenase concentrations (C1 and C2 collagenase) and optimal ratio of solution volume (mLs) to bone fragment weight (mgs) are determined.

According to the process, fragments of VB bone are placed in cryoprotectant solution comprised of PLASMA-LYTE™, 2.5% human serum albumin and 10% dimethyl sulfoxide (DMSO) and incubated for 1 hour at 4° C. The solution is removed and the bone fragments cooled at a rate of to ~86° C. and then plunged into liquid nitrogen. After 24-48 hours in liquid nitrogen, the bone fragments are thawed rapidly in a water bath set at 37° C. and then washed in saline and digested using the collagenase/protease solution described above.

The optimal volume-to-weight ratio has been found to be 5:1 at an optimal incubation time of 2.5 hours. The optimal protease produced neutral protease activity of 19.6 U/mL. On the other hand, it was found that total viable MSC cell count is generally insensitive to collagenase concentration. It was also found that the yields produced by recombinant collagenase isoforms C1 and C2 are similar to the yields with purified collagenase, regardless of the C1/C2 ratio. Further details of the MSC recovery process of the present disclosure are found in the technical article in Appendix A to the present application, the entire disclosure of which is incorporated herein by reference.

Predicting Cell Viability Based on Ischemia Time

As discussed above, ischemia time of the donor bone impacts the viability of the cells extracted using the processes described above. According to the present disclosure, total ischemia is defined as the interval starting at time of death (the point at which the donor's arterial system was cross-clamped and circulation ceased) and ending with the start of the recovery of cells from the bone. For purposes of statistical modeling, this total interval can be separated into three successive and mutually exclusive time components: (a) Warm Ischemia Time (WIT)—beginning at time of death and ending either when bones are recovered and packed on ice or when the body is placed in a cooler; (b) Body Cooling Time (BCT)—beginning when the body is placed in the cooler and ending when bones are packed on ice; and (c) Cold Ischemia Time (CIT)—beginning when bones are packed on ice and ending when processing begins for extraction of cells, such as HSPCs. Thus, Total Ischemia Time=(WIT)+(BCT)+(CIT). For cases where whole-body cooling is not used, BCT is zero and Total Ischemia Time= (WIT)+(CIT).

In addition to Total Ischemia Time, a variable corresponding to processing experience can be incorporated into the viability determination. It is known that learning curves exert significant effects on outcomes, so to control for this fact a variable EXP can be defined as the number of donors processed prior to the current donor—i.e., for the $i^{th}$ donor, EXP=i−1. Other variables can include bone type (such as vertebral bodies and ilia), donor sex and donor age.

In one aspect, the outcome variables are: the proportion of a particular cell population, such as CD34+ cells, that are viable, the total number of colony forming units (CFUs) per $10^5$ nucleated cells detected following cell processing, and the number of CFU granulocyte macrophages (CFU-GM) detected per $10^5$ nucleated cells.

According to the present disclosure, an ordinary least squares (OLS) beta regression model can be used to predict the outcome variables, with linear regression models used for CFU and CFU-GM and a beta regression model used for the proportion of viable CD34+ cells, or % CD34+, where 0<(% CD34+)<1. The beta regression equation for predicting % CD34+ is:

$$\eta = \ln[pCD34^*/(1-pCD34^*)] = \beta_0 + \beta_1(WIT) + \beta_2(BCT) + \beta_3(BCT^2) + \beta_4(CIT) + \beta_5(CIT^2) \quad (1)$$

Where:
$pCD34^* = [1+100(\% \ CD34+)]/102$, which is a transformation of the variable of interest
$\beta_0$=Constant (intercept)
$\beta_1$=Coefficient associated with warm ischemia time (WIT)
$\beta_2$=Coefficient associated with body cooling time (BCT)
$\beta_3$=Coefficient associated with body cooling time squared ($BCT^2$)
$\beta_4$=Coefficient associated with cold ischemia time (CIT)
$\beta_5$=Coefficient associated with cold ischemia time squared ($CIT^2$)

An inverse link function is applied to the linear predictor $\eta$ so that the result is the expected value of the outcome variable $pCD34^*$, namely the percentage of viable CD34+ cells expected to be extracted from the donor bone. The inverse link function is:

$$E[pCD34^*] = \frac{\exp(\eta)}{[1+\exp(\eta)]} \quad (2)$$

or substituting Equation (1) above for $\eta$:

$$E[pCD34^*] = \frac{\exp(\eta)}{[1+\exp(\eta)]} = \frac{\exp[\beta_0 + \beta_1(X_1) + \beta_2(X_2) + \beta_3(X_3) + \beta_4(X_4) + \beta_5(X_5)]}{\left[\begin{array}{c} 1 + \exp(\beta_0 + \beta_1(X_1) + \beta_2(X_2) + \\ \beta_3(X_3) + \beta_4(X_4) + \beta_5(X_5)) \end{array}\right]} \quad (3)$$

In this embodiment, the mathematical model predicts the proportion of viable CD34+ cells that can be extracted from the donor bone that has been subjected to the specific ischemia conditions. The value of $E[pCD34^*]$ is between 0 and 1 since it is the ratio of the number of viable CD34+ cells to the total number of CD34+ cells in the bone sample.

In one embodiment, the coefficients for the beta regression calculation of the predicted % CD34+ have the following values:
$\beta_0$=3.5000
$\beta_1$=−0.01996
$\beta_2$=−0.181
$\beta_3$=0.007
$\beta_4$=−0.111
$\beta_5$=0.002
where each of the beta coefficients $\beta_0$, $\beta_1$, $\beta_2$, $\beta_3$, $\beta_4$, $\beta_5$ correspond to the intercept, WIT, BCT, $BCT^2$, CIT and $CIT^2$, respectively, as described above.

The predictions for the total colony forming units CFU and the number of CFU granulocyte microphages CFU-GM can be obtained using the following linear regression model:

$$\eta = \beta_0 + \beta_1(WIT) + \beta_2(BCT) + \beta_3(BCT^2) + \beta_4(CIT) \quad (4)$$

The linear regression model used to determine the CFU outcome variable can have the following coefficient values:
$\beta_0$=756.5084
$\beta_1$=−9.10826
$\beta_2$=−95.03639
$\beta_3$=3.45603
$\beta_4$=−4.53349, where each of the beta coefficients $\beta_0$, $\beta_1$, $\beta_2$, $\beta_3$, $\beta_4$ correspond to the intercept, WIT, BCT, BCT$^2$ and CIT, respectively, as described above.

The linear regression model used to determine the CFU-GM outcome variable can have the following form:

$$\eta=\beta_0+\beta_1(WIT)+\beta_2(BCT)+\beta_3(CIT) \quad (5)$$

with the following coefficient values:
$\beta_0=104.1805$
$\beta_1=-8.11295$
$\beta_2=-5.52927$
$\beta_3=0.08872$.

The foregoing models are base or un-adjusted models that only account for the ischemia-based variables and not the experience, bone type, donor sex and donor age variables. A fully adjusted model for % CD34+ that accounts for all of the variables can have the following form:

$$\eta=\beta_0+\beta_1(Experience)+\beta_2(Bone\ Type)+\beta_3(WIT)+\beta_4(BCT)+\beta_5(BCT^2)+\beta_6(CIT)+\beta_7(CIT^2) \quad (6)$$

with the following respective values for the coefficients:

| %CD34+ | |
| --- | --- |
| $\beta_0$ Constant | 3.112681 |
| $\beta_1$ Experience | 0.0095651 |
| $\beta_2$ Bone Type (VB = 1) | 0.0351495 |
| $\beta_3$ Warm Ischemia (WIT) (hrs)$^a$ | −0.0229737 |
| $\beta_4$ Body Cooling (BCT) (hrs) | −0.176881 |
| $\beta_5$ Body Cooling Squared (BCT$^2$) | 0.0062293 |
| $\beta_6$ Cold Ischemia (CIT) (hrs) | −0.101344 |
| $\beta_7$ Cold Ischemia Squared (CIT$^2$) | 0.0013874 |

The fully adjusted model for CFU is as follows:

$$\eta=\beta_0+\beta_1(Experience)+\beta_2(Facility\times Experience)+\beta_3(Bone\ Type)+\beta_4(WIT)+\beta_5(BCT)+\beta_6(BCT^2)+\beta_7(CIT)+\beta_8(CIT^2) \quad (7)$$

| CFU | |
| --- | --- |
| $\beta_0$ Constant | 160.6034 |
| $\beta_1$ Experience | 2.60499 |
| $\beta_2$ Facility x Experience | 5.36988 |
| $\beta_3$ Bone Type (VB = 1) | 206.9969 |
| $\beta_4$ Warm Ischemia (hrs) | −3.73481 |
| $\beta_5$ Body Cooling (hrs) | −82.49506 |
| $\beta_6$ Body Cooling Squared | 2.95994 |
| $\beta_7$ Cold Ischemia (hrs) | 9.55975 |
| $\beta_8$ Cold Ischemia Squared | −0.12535 |

The coefficient $\beta_1$ attempts to quantify the effect of the number of donors processed (i.e., experience) on cell quantity and viability. In the fully adjusted CFU model, coefficient $\beta_2$ corresponds to the experience at a particular facility based on the assumption that facilities can have different learning trajectories. Either or both of these coefficients may be modified or even eliminated.

| CFU-GM | |
| --- | --- |
| $\beta_0$ Constant | 88.3589 |
| $\beta_1$ Bone Type (VB = 1) | 16.71592 |
| $\beta_2$ Warm Ischemia (hrs) | −7.19329 |
| $\beta_3$ Body Cooling (hrs) | −5.24410 |
| $\beta_4$ Cold Ischemia (hrs) | 0.10750 |

Applying these models to observed data can be used to determine the effect of ischemia time variables on % CD34+, as reflected in the tables shown in FIGS. 12A-12C, on total CFU, as shown in the tables of FIGS. 13A-13C, and on the amount of CFU-GM, as shown in the tables of FIGS. 14A-14C. The data in these tables can be used to decide whether a particular donor bone can yield sufficient cells to warrant further processing of the donor bone. In other words, the predictive models can be used to establish ischemia tolerance limits and HSPC quality acceptance criteria. For instance, with respect to the % CD34+ outcome variable, predicted values of over 80% may be required in order to consider the particular donor bone.

The models described above and the examples shown in the tables of FIGS. 12a-14C suggest that acceptable levels of HSPC quality are achievable despite the prolonged ischemia times that are inevitable when bones must be procured by geographically-dispersed OPOs and shipped long distances to processing centers. Even under such conditions, favorable combinations of warm- and cold-ischemia times can be achieved, enabling % CD34+ viabilities in the range of 80-90%. The models also suggest that refrigerating the body prior to bone recovery, a practice that is common in the recovery of tissues, is less beneficial in the context of bone marrow recovery. For instance, when whole-body cooling was used, CD34+ viability averaged 72.75%, whereas when body cooling was not used, the average was just under 90%. These models suggest that an optimal practice would be to dispense with body cooling and move recovered bone as quickly as possible to a cold ischemic environment. The models further suggest that limiting WIT (warm ischemia time) to less than eight (8) hours and CIT (cold ischemia time) to less than 40 hours optimizes the opportunity to recover meaningful quantities of viable cells from donor bone.

Figure 15:
FIG. 15 is a chart of viability threshold as a function of warm ischemia times and cold ischemia times.

The models disclosed herein predict viability according to the chart shown in FIG. 15 in which an 80% CD34+ cell viability threshold is determined to be acceptable. As reflected in the chart, the relationship between warm and cold ischemia times follows a curve from a point at which the WIT is 10 hours and the CIT is 18 hours, to a point at which the WIT is 1 hour and the CIT is 27 hours.

Further details of the method for predicting cell viability of the present disclosure are found in Appendix B to the present application, the entire disclosure of which is incorporated herein by reference.

The present disclosure should be considered as illustrative and not restrictive in character. It is understood that only certain embodiments have been presented and that all changes, modifications and further applications that come within the spirit of the disclosure are desired to be protected.

What is claimed is:

1. A method for manipulating environmental conditions of a cadaver such that stem cells obtained from bone explanted from the cadaver comprise CD34+ cells, among which at least 70% of the recovered CD34+ cells are viable, the method comprising steps of:
   (1) identifying a human who is nearing death;
   (2) recording the time of death of the human, at this time the human becomes a cadaver;
   (3) placing the cadaver or an explanted bone from the cadaver into a cooling environment;
   (4) recording the time when step (3) occurs;
   wherein the period of time from step (2) to step (3) is referred to as the warm ischemia time (WIT) and step (3) is performed from no less than about one-half to no more than about eight hours after step (2);
   (5) processing the cadaver bone for extraction of stem cells; and (6) recording the time when step (5) begins;
wherein the period of time from step (3) to step (5) is referred to as the cold ischemia time (CIT) and step (5) is performed from no less than about seven hours to no more than about thirty-nine and one-half hours after step (3);
wherein WIT and CIT are distinct periods of time;
wherein the sum of WIT and CIT is forty hours or less such that
when the WIT is more than one-half hour, the CIT is no more than thirty-nine and one-half hours and
when the WIT is about eight hours, the CIT is no more than thirty-two hours; and
wherein the stem cells comprise CD34+ cells, among which at least 70% of the recovered CD34+ cells are viable
wherein when the sum of WIT and CIT is greater than forty hours and/or WIT is greater than eight hours and/or CIT is greater than about thirty-nine and one-half hours, fewer recovered CD34+ cells will be viable when compared to when the sum of WIT and CIT is forty hours or less and/or WIT is from no less than about one-half to no more than about eight hours and/or CIT is from no less than about seven hours to no more than about thirty-nine and one-half hours.

2. The method of claim 1, wherein the method provides at least about 10 to about 350 CFU-Total, wherein, CFU-Total is the total number of colony forming units (CFUs) per $10^5$ nucleated cells detected.

3. The method of claim 1, wherein the method provides at least about 10 to about 100 CFU-GM, wherein CFU-GM is the number of CFU granulocyte macrophages detected per $10^5$ nucleated cells.

4. The method of claim 1, wherein the cadaver bone is derived from a vertebral body, an ileum, or a combination thereof.

5. The method of claim 4, wherein the cadaver bone is derived from a plurality of cadaver bones from the same donor.

6. The method of claim 1, wherein the recovered stem cells comprise hematopoietic stem cells (HSCs).

7. The method of claim 1, wherein the recovered stem cells comprise mesenchymal stem cells (MSCs).

8. The method of claim 1, wherein at least 85% of the recovered CD34+ cells are viable.

9. The method of claim 1, wherein the Body Cooling Time (BCT) is less than about four hours, wherein the BCT begins when the cadaver is placed in a cooling environment and ends when cadaver bone is placed in a cooling environment or conditions;
wherein BCT only occurs when a cadaver is placed into a cooling environment and an explanted bone is extracted from the cooled cadaver.

10. The method of claim 9, wherein the BCT is less than about 1 hour.

11. The method of claim 10, wherein the BCT is about zero hours.

12. The method of claim 11, wherein at least 90% of the recovered CD34+ cells are viable.

13. The method of claim 9, wherein at least 85% of the recovered CD34+ cells are viable.

14. The method of claim 1, wherein the total ischemia time comprising the sum of WIT, CIT, and Body Cooling Time (BCT) is less than about forty hours, wherein the BCT begins when the cadaver is placed in a cooling environment and ends when cadaver bone is placed in a cooling environment or condition
wherein BCT only occurs when a cadaver is placed into a cooling environment and an explanted bone is extracted from the cooled cadaver.

15. The method of claim 14, wherein the BCT is less than one hour.

16. The method of claim 15, wherein the BCT is about zero hours.

17. The method of claim 16, wherein at least 90% of the recovered CD34+ cells are viable.

18. The method of claim 14, wherein at least 85% of the recovered CD34+ cells are viable.

19. The method of claim 1, wherein
when the WIT is more than one hour, the CIT is no more than thirty-nine hours,
when the WIT is more than one and one-half hours, the CIT is no more than thirty-eight and one-half hours,
when the WIT is more than two hours, the CIT is no more than thirty-eight hours,
when the WIT is more than two and one-half hours, the CIT is no more than thirty-seven and one-half hours,
when the WIT is more than three hours, the CIT is no more than thirty-seven hours,
when the WIT is more than three and one-half hours, the CIT is no more than thirty-six and one-half hours,
when the WIT is more than four hours, the CIT is no more than thirty-six hours,
when the WIT is more than four and one-half hours, the CIT is no more than thirty-five and one-half hours,
when the WIT is more than five hours, the CIT is no more than thirty-five hours,
when the WIT is more than five and one-half hours, the CIT is no more than thirty-four and one-half hours,
when the WIT is more than six hours, the CIT is no more than thirty-four hours, and
when the WIT is more than six and one-half hours, the CIT is no more than thirty-three and one-half hours,
when the WIT is more than seven hours, the CIT is no more than thirty-three hours, and
when the WIT is more than seven and one-half hours, the CIT is no more than thirty-two and one-half hours.

\* \* \* \* \*